(12) United States Patent
Benecke et al.

(10) Patent No.: US 8,309,676 B2
(45) Date of Patent: Nov. 13, 2012

(54) FORMALDEHYDE FREE BINDERS

(75) Inventors: Herman P. Benecke, Columbus, OH (US); Daniel B. Garbark, Blacklick, OH (US); Alex W. Kawczak, Dublin, OH (US); Michael C. Clingerman, Hilliard, OH (US)

(73) Assignee: Battelle Memorial Institute, Columbus, OH (US)

( * ) Notice: Subject to any disclaimer, the term of this patent is extended or adjusted under 35 U.S.C. 154(b) by 162 days.

(21) Appl. No.: 12/615,317

(22) Filed: Nov. 10, 2009

(65) Prior Publication Data

US 2010/0081774 A1    Apr. 1, 2010

Related U.S. Application Data

(62) Division of application No. 12/009,199, filed on Jan. 16, 2008, now Pat. No. 7,638,592.

(60) Provisional application No. 60/880,669, filed on Jan. 16, 2007.

(51) Int. Cl.
*C08G 69/44* (2006.01)

(52) U.S. Cl. ........ 528/291; 528/271; 528/272; 528/288; 528/292; 528/310; 528/422; 427/372.2; 549/200

(58) Field of Classification Search ............... 528/291, 528/292, 288, 272, 302, 310, 422, 271; 442/180, 442/300, 304, 394; 427/393.5, 372.2; 428/423.1; 521/129, 94, 156, 167; 549/6, 200
See application file for complete search history.

(56) References Cited

U.S. PATENT DOCUMENTS

| | | | | |
|---|---|---|---|---|
| 4,493,909 A | * | 1/1985 | Haas et al. | ............ 521/166 |
| 5,143,582 A | | 9/1992 | Arkens et al. | |
| 5,459,183 A | | 10/1995 | Taylor et al. | |
| 5,534,612 A | | 7/1996 | Taylor et al. | |
| 2002/0160677 A1 | * | 10/2002 | Loffler et al. | ............ 442/180 |
| 2007/0123679 A1 | | 5/2007 | Swift et al. | |
| 2007/0123680 A1 | | 5/2007 | Swift et al. | |
| 2007/0142596 A1 | | 6/2007 | Swift et al. | |

FOREIGN PATENT DOCUMENTS

GB      1451744    * 10/1975

* cited by examiner

*Primary Examiner* — Frances Tischler
(74) *Attorney, Agent, or Firm* — Yimei C. Hammond; Kremblas & Foster

(57) ABSTRACT

New polyols; oligomers, and polymers made from the polyols; and binders made from the new polyols, oligomers, or polymers that can be used in binders, where the binders typically include one or more polyols, and a polyfunctional acid or a polyfunctional nitrile.

7 Claims, No Drawings

FORMALDEHYDE FREE BINDERS

This application is a divisional application of the U.S. application Ser. No. 12/009,199, filed on Jan. 16, 2008, now U.S. Pat. No. 7,638,592; which claims the benefits of U.S. Provisional Application 60/880,669 filed on Jan. 16, 2007. The contents of the two applications are incorporated herein by reference.

FIELD OF THE INVENTION

This invention relates to new heat curable aqueous composition that can function as a binder in various types of composites. In one aspect, the invention is useful as a binder in the manufacture of consolidated glass fibers or other non-woven fiber systems. In another aspect, the binder allows the fibers to be strongly bound and interconnected to each other in a three dimensional matrix to impart mechanical strength and product rigidity. In another aspect the inventive compositions are essentially free of formaldehyde.

BACKGROUND OF THE INVENTION

Alkaline phenol-formaldehyde aqueous-based binders are used to bind fiberglass fibers together to generate a tightly bound system after thermal curing. Alkaline phenol-formaldehyde binders may also contain an excess of formaldehyde and these systems are typically extended by using relatively inexpensive urea that is incorporated in the cured resin. The degree of polymerization of these resins is sufficiently advanced to provide appropriate viscosity and cure profiles. These binder solutions and relatively short segments of narrow diameter glass fibers are typically co-deposited on a continuous conveyor belt with the aid of a vacuum that is drawn through the mat. These type resins are typically cured within 1-1.5 minutes at about 400° F. within air-blown ovens where evaporation of water occurs initially and the resin is at about 400° F. for only about 20 seconds. Under these conditions, evaporation of water initially occurs and this is followed by curing of the phenol formaldehyde binder to a crosslinked state. These binder solutions tend to accumulate at the glass fiber touching points within the fiberglass matrix which leads to effective binding of glass fibers to each other at these points to generate a tightly bound three dimensional system. Relatively low initial resin viscosities coupled with production of a rigid cured resin are desired since these properties allow expansion of the fiberglass matrix when the cured fiberglass mat exits the curing oven in a compressed state. Attaining a high degree of expansion after the cured mat exits the oven is important in achieving a highly insulating material as measured by relatively high R values. Also, a rigidly bound system will allow compression for packaging and shipping and expansion to nearly the original dimensions after removal from the shipping wrapping.

Fiberglass mats prepared from phenol-formaldehyde or phenol-urea-formaldehyde resins are typically used for insulation and molded media and structural board in residential and commercial applications. Use of these materials in these environments can cause significant health effects since the materials are known to slowly release formaldehyde that is a known toxic substance. Hence, many alternate binder resin compositions have been proposed and (or) are in use that do not incorporate formaldehyde. It is also highly desirable that any replacement resin be water-borne to avoid solvent emissions during manufacturing.

Many of these replacement resins are aqueous compositions of polymeric carboxylic acids and polyols that undergo thermal curing by esterification of the polymeric carboxylic acid with the polyol to generate a three dimensional crosslinked polyester system. U.S. Pat. Nos. 5,318,990 and 5,763,524 describe aqueous solutions of polymeric carboxylic acids such as polyacrylic acid (PAA) that are esterified with trihydric polyols such as glycerin (glycerol) or trimethylolpropane while using a salt of a phosphorous containing acid such as sodium hypophosphite as a catalyst. U.S. Pat. No. 6,274,661 describes an aqueous solution of a polymeric carboxylic acid, a trihydric alcohol, a salt of phosphorous containing acid, and various corrosion inhibitors. In the systems described above, a corrosion inhibitor is desirable since the binder solutions are generally acidic which can cause erosion of carbon steel components of the thermal curing system. A variety of other binder compositions containing polymeric carboxylic acids and polyols are described in U.S. Pat. Nos. 6,221,973; 6,699,945; 6,734,2237; 6,818,694; 6,884,838; and 6,884,849. Binder compositions containing polymeric carboxylic acids and activated polyols such as beta-hydroxyethylamides are described in U.S. Pat. Nos. 5,143,582; 5,340,868 and 6,221,973.

Whereas these polyester binders prepared from the esterification of polymeric carboxylic acids and polyols do not liberate formaldehyde during curing or use, major deficiencies still exist in polyester binders. One is that their curing times are relatively long; leading to decreased production rates of cured fiberglass mats. Decreased production rates require larger or increased number of production lines to produce the required amount of cured fiberglass mat, typically resulting in increased capital and plant operating costs. Another deficiency of polyester binders is the relatively low pH (corresponding to relatively high acidities) of these systems caused by the required high concentrations of carboxylic acid functionality. Low binder pH can cause significant erosion of binder curing equipment and facilities unless this equipment is composed of high quality steel to prevent corrosion. Another deficiency of cured polyester binders is their relatively high flammability since they are produced from combustible aliphatic polymeric carboxylic acids and polyols.

BRIEF DESCRIPTION OF THE INVENTION

Broadly, the invention provides for new polyols that can be reacted to produce oligomers useful for making polymers typically for binder applications. The oligomers typically have repeat units disclosed herein of about 1 to 20 repeating units. The polymers typically have repeating units of about 1 to about 100,000, being most typically above 20 repeating units. The new binders are typically formed at fast rates of reaction.

A first polyol having the Formula I, is disclosed

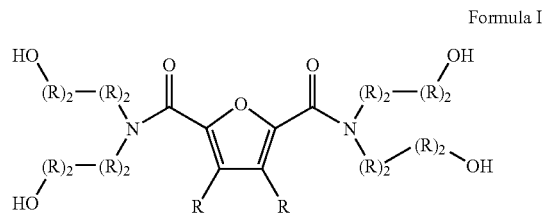

Formula I wherein each R is the same or different, each $(R)_2$ represents two radicals R that are the same or different, R can be hydrogen, hydroxy, alkyl of 1-12 carbon atoms, hydroxyalkyl, halogen, halogenalkyl, salts, aryl, cycloalkyl, heteroaromatic (I.e. furanic), amines, carboxy, carboalkoxy, vinyl, substituted vinyl, ether, alkyl ether, alkene, alkyne, aldehyde, carbonate, ester, and carboxamide.

A second polyol having the Formula II, is disclosed

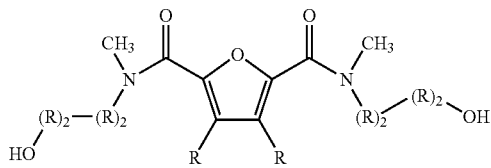

Formula II wherein each R is the same or different, each (R)₂ represents two radicals R that are the same or different, R can be hydrogen, hydroxy, alkyl of 1-12 carbon atoms, hydroxyalkyl, halogen, halogenalkyl, salts, aryl, cycloalkyl, heteroaromatic (I.e. furanic), amine, carboxy, carboalkoxy, vinyl, substituted vinyl, ether, alkyl ether, alkene, alkyne, aldehyde, carbonate, ester, and carboxamide.

A third polyol having the Formula III, is disclosed

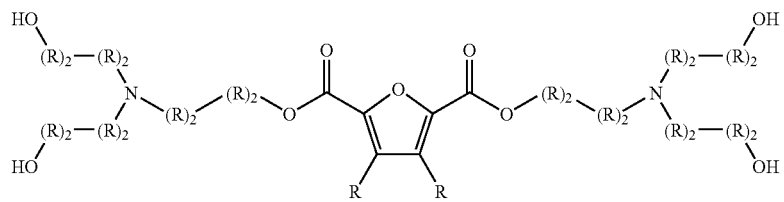

Formula III wherein each R is the same or different, each (R)₂ represents two radicals R that are the same or different, R can be hydrogen, hydroxy, alkyl of 1-12 carbon atoms, hydroxyalkyl, halogen, halogenalkyl, salts, aryl, cycloalkyl, heteroaromatic (I.e. furanic), amine, carboxy, carboalkoxy, vinyl, substituted vinyl, ether, alkyl ether, alkene, alkyne, aldehyde, carbonate, ester, and carboxamide.

A fourth polyol having the Formula IV, is disclosed

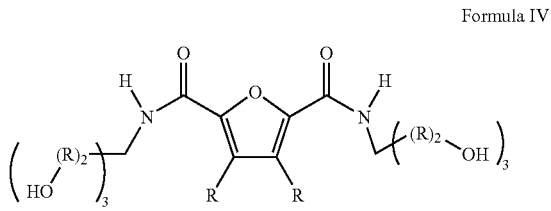

Formula IV wherein each R is the same or different, each (R)₂ represents two radicals R that are the same or different, R can be hydrogen, hydroxy, alkyl of 1-12 carbon atoms, hydroxyalkyl, halogen, halogenalkyl, salts, aryl, cycloalkyl, heteroaromatic (I.e. furanic), amine, carboxy, carboalkoxy, vinyl, substituted vinyl, ether, alkyl ether, alkene, alkyne, aldehyde, carbonate, ester, and carboxamide.

A fifth polyol having the Formula V, is disclosed

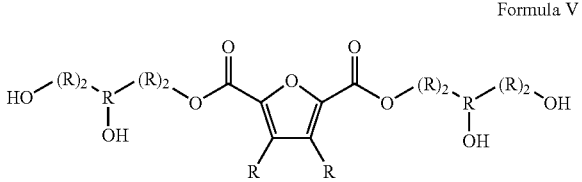

Formula V wherein each R is the same or different, each (R)₂ represents two radicals R that are the same or different, R can be hydrogen, hydroxy, alkyl of 1-12 carbon atoms, hydroxyalkyl, halogen, halogenalkyl, salts, aryl, cycloalkyl, heteroaromatic (I.e. furanic), amine, carboxy, carboalkoxy, vinyl, substituted vinyl, ether, alkyl ether, alkene, alkyne, aldehyde, carbonate, ester, and carboxamide.

The polyols may be provided as a mixture of two or more polyols selected from the polyols of Formula I-V. Alternatively, the polyols may be provided as a mixture of two or more polyols selected from the polyols of Formula III to V.

The polyols of Formula I to V are typically reacted to form oligomers that can be further polymerized into binders such an oligomer that is the reaction product of one or more polyols selected from the group consisting polyols according to Formula I, Formula II, Formula III, Formula IV, and Formula v; and a polyfunctional acid or a polyfunctional nitrile. Alternatively, the polyols of Formula III to V are typically reacted to form oligomers that can be further polymerized into binders such an oligomer that is the reaction product of one or more polyols selected from the group consisting of polyols according to Formula III, Formula IV, and Formula V; and a polyfunctional acid or a polyfunctional nitrile.

In the foregoing Formulas I to V, the number of carbon atoms in the R groups are typically up to about 12. In some embodiments the R group is typically hydrogen, or an alkyl of 1-12 carbon atoms.

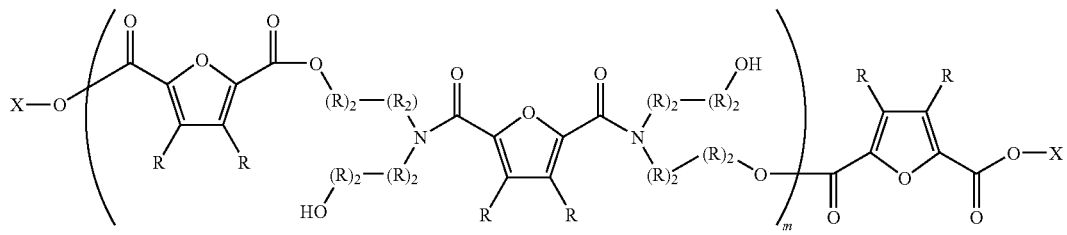

wherein X is a hydrogen, an anhydride group, an aliphatic group, a cycloaliphatic group, an aromatic group, a heteroaromatic group, a metal salt, or a beta-hydroxyl amide repeating unit;

wherein each R is the same or different, each (R)$_2$ represents two radicals R that are the same or different, R can be hydrogen, hydroxy, alkyl of 1-12 carbon atoms, hydroxyalkyl, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, and carboxamide; and wherein m is typically an integer from 1 to 100,000. In some embodiments the repeat unit m ranges from 1 up to where the polymer is not longer water soluble. In yet other embodiments m ranges from 1 to about 1000, and in yet others from 1 to 100. The polymer typically contains carboxy groups or carboxylic anhydride groups or salts of the carboxy groups, and a beta-hydroxyalkyl amide. Preferably, in obtaining a higher weight polymer the repeat unit m is above that where an oligomer is obtained, typically above 20 repeating units.

An additional embodiment includes a new polyol selected from polyol 1, polyol 2, polyol 3, polyol 4, and polyol 5

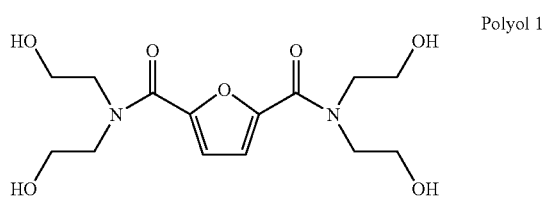

Polyol 1

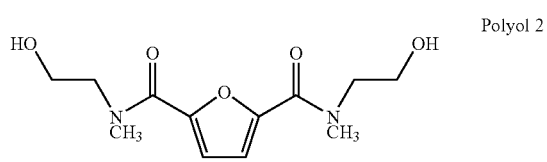

Polyol 2

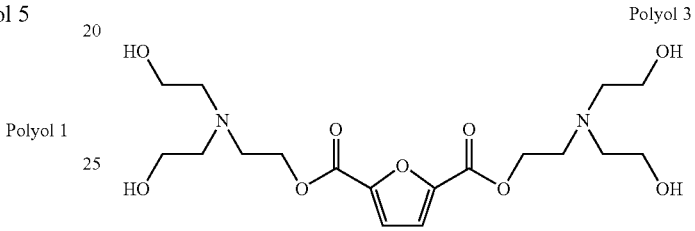

Polyol 3

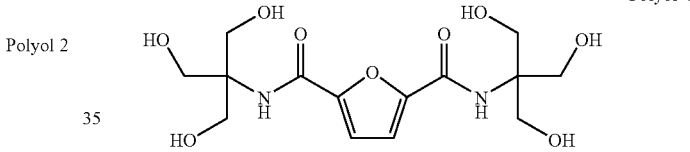

Polyol 4

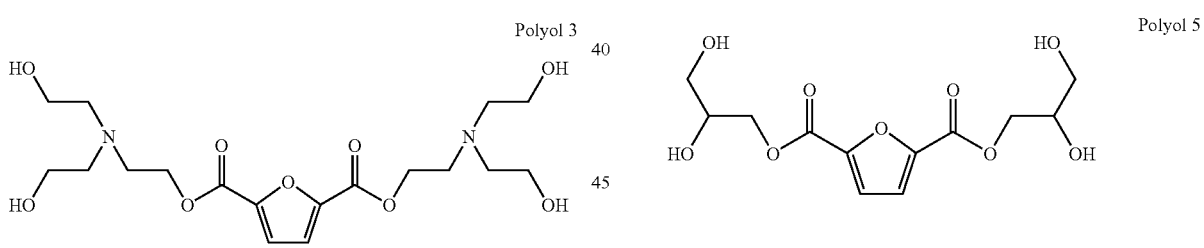

Polyol 5

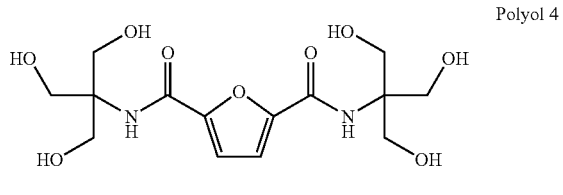

Polyol 1

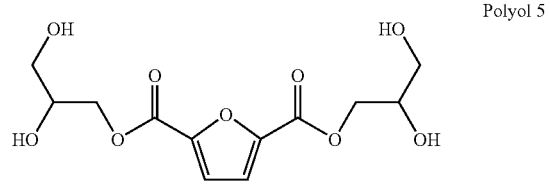

Polyol 2

A further embodiment includes a mixture of polyols from two or more polyols selected from the group consisting of A yet further embodiment provides a composition typically used for binders that is an oligomer or polymer of a reaction product of
a. one or more polyols selected from the group consisting polyol 1, polyol 2, polyol 3, polyol 4, and polyol 5; and
b. a polyfunctional acid or a polyfunctional nitrile. In one embodiment the polyfunctional acid is a diacid. Typically the polyfunctional acid is selected from the group of acids consisting of FDCA, malic acid, citric acid, maleic acid, oxalic acid, malonic acid, succinic acid, itaconic acid, fumeric acid, and mixtures thereof.

Another embodiment provides for a composition that is the reaction product of
a. FDCA bisamide of diethanolamine, and FDCA methyl ester/monoamide of diethanolamine; or
b. FDCA bisamide of diethanolamine, mixed bisamide of diethanolamine; 2-(methylamino)ethanol, and the mixed FDCA amide/methyl ester.

Typically cure time for the binder according to the invention can be reduced by the steps of a. mixing a polyol selected from polyol 1 through 5, or an oligomeric reaction product thereof with a polyfunctional acid, and optionally a catalyst; and b. curing the mixture with heat to obtain the reduced cure time.

Another embodiment provides for a binder that is polymeric reaction product from a mixture of two or more such polyols, or oligomeric reaction product is prepared from two or more such polyols.

Typically acidity in a binder formulation can be reduced by mixing either a polyol selected from polyol 1 through 5 or an oligomer of polyol selected from polyol 1 through polyol 5 with a polyfunctional acid, and optionally a catalyst.

DETAILED DESCRIPTION OF THE INVENTION AND BEST MODE

Broadly the invention provides for new polyols. The polyols provide useful and new applications as binders for various applications including composites. The novel binders are based on polyols that are synthesized from or contain furan-2,5-dicarboxylic acid (FDCA). FDCA is typically derived from the cyclization of fructose and hence can be derived form renewable and sustainable materials. FDCA is very water insoluble, unless it is converted to its salts, and the hydroxyl functionality in these polyols was expected to provide water solubility. Typical polyol binders are prepared for curing with polyfunctional acids (e.g. without limitation polyacrylic acid (PAA)) and are shown in polyol formulas Polyol 1 through Polyol 5 below:

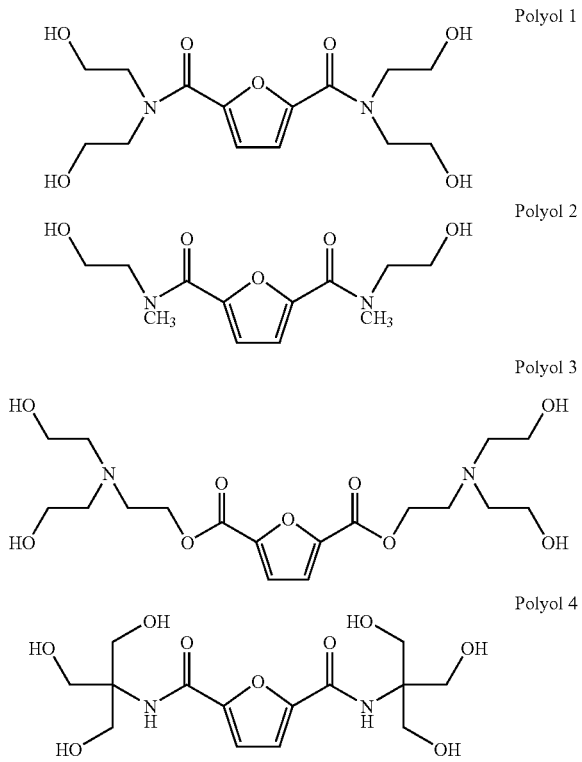

-continued

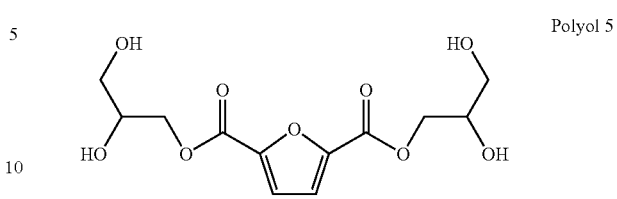

Polyol 5

Polyols 1 and 2 contain tertiary beta-hydroxyethylamide groups that have been demonstrated to undergo esterification reactions faster than certain other primary alcohol groups (Z. W. Wicks, Jr., M. R. Appelt, and J. C. Soleim, J. Coatings Technology, 57, No. 726 (1985)). Polyol 3 is a diester of FDCA and triethanolamine that has two tertiary amine groups that help decrease the acidity of compositions containing carboxylic acids. Polyol 4 is a bisamide of FDCA and tris (hydroxymethyl)aminomethane (Tris) and polyol 5 is a diester of FDCA and glycerin. Polyols 1, 3, 4, and 5 have four or more hydroxyl groups and thus can participate in crosslinking reactions with carboxylic acids more effectively than polyol 2 which has only two available hydroxyl groups.

Binder compositions were evaluated in a preliminary fashion by adding specific amounts to the surface of a hot plate heated to about 180° C. at time zero in these tests in stroke/cure tests. Pools of binder mixtures were stroked back and forth in a regular fashion with a spatula and the time needed to first attain a viable and self-supporting string was recorded as well as the time at which the entire mass solidified into a tight mass. In the data tables, these times are recorded as the string and cure times.

One type aqueous binder solution was prepared by mixing polyols 1-5 directly with polyfunctional acids such as PAA. Another type binder solution was obtained by pre-converting polyols to polyol-based oligomers by pre-reaction with diacids through esterification reactions. The main oligomers described herein are derived from polyol 1 and FDCA but some data is provided for oligomers derived from polyol 1 and malic acid as well as polyol 2 and malic acid. Limited esterification rate studies suggest that beta-hydroxyethylamides undergo esterification reactions faster the higher the acidity of the carboxylic acid. Since FDCA is unusually acidic, evidenced by its $pK_a$ of 2.6, whereas benzoic and octanoic acids have $pK_a$ values of 4.2 and 4.9 respectively, it was possible that polyols 1 and 2 would react with FDCA to form oligomeric resins significantly faster than other compounds containing primary alcohol functionality.

Immediately below is hypothetical Structure 1 of an oligomer formed by the esterification of FDCA with a 20% molar excess of polyol 1. Note that Structure 1 also illustrates crosslinking between FDCA and polyol 1. This structure is exemplary of the type of oligomerization that can be obtained from reactions with polyol 1, polyol 3, polyol 4 and polyol 5, or mixtures thereof. However, polyol 2 can only form a linear oligomer with FDCA.

Structure 1

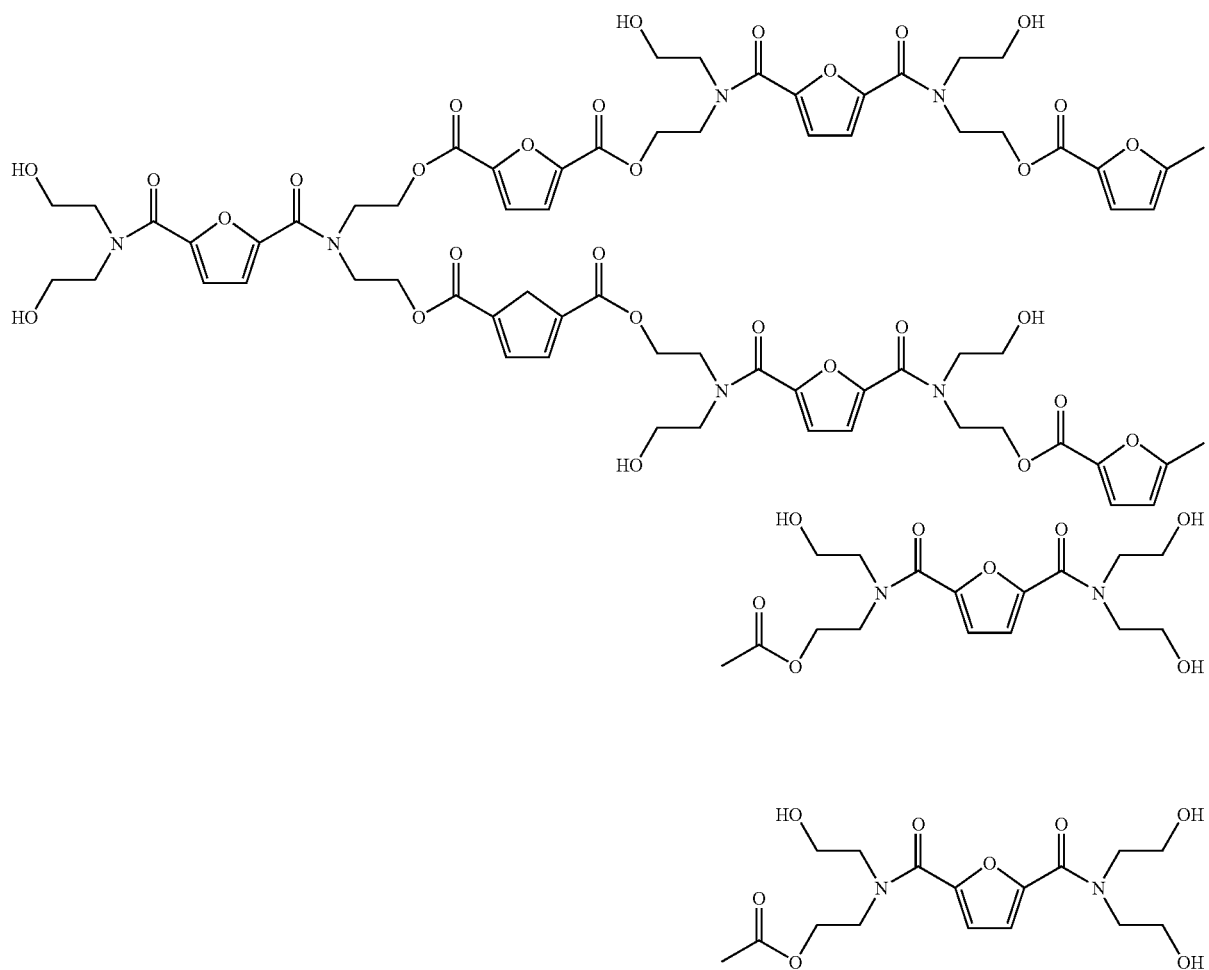

From Structure 1 It can be seen that the greater the excess of polyol 1 relative to FDCA, the greater the amount of free hydroxyl groups that will be available in the oligomer for subsequent curing reaction with polyacids such as PAA. In addition, oligomers containing an excess of polyol 1 relative to the quantity of FDCA were expected to have higher water solubilities due to the increased proportion of water-solubilizing hydroxyl groups in these oligomers. Another consideration in preparing these type oligomers is the amount of unreacted and residual carboxylic acid functionality that was not consumed in esterification reactions. Such residual carboxylic acid groups will unfavorably contribute to the acidity of binder compositions. On the other hand, driving these esterification reactions to completion can cause increased crosslinking which can lead to reduced oligomer aqueous solubilities. Attaining the most favorable balance of these oligomer properties will be primarily influenced by the oligomerization reaction time, temperature, and mixing conditions.

Oligomers of polyol 1 and polyol 2 were condensed with polyacids such as PAA to prepare cured binder systems. Preparation of this type oligomer represents a type of pre-curing which can result in binder final stage curing times being decreased compared to the curing times involved when reacting polyols 1 and 2 themselves with PAA. Also, this type oligomer generally will have increased and adjustable viscosities compared to polyols 1-5 that will aid in the binder properly wetting and adhering to fiberglass or other non-woven fibers during the initial stages of curing. Oligomer viscosities can be increased or decreased as needed by adjusting reaction times and temperatures as well as polyol/FDCA ratios. Another advantage of preparing this type oligomer is that it increases the proportion of biobased and sustainable FDCA in the final binder composition and correspondingly reduces the amount of petrochemical-derived PAA in the final binder composition. Also, since some of the hydroxyl groups of various polyols will already have been pre-reacted with FDCA, less PAA will be needed, thus reducing the acidity and increasing the pH of starting binder composition.

Binder compositions were formulated for testing in the following manner. After dispensing quantities of any one polyol, specific amounts of a 25% aqueous solution of 100,000 weight average molecular weight PAA was added so that the ratio of moles of carboxylic acid groups provided by PAA to the moles of hydroxyl groups in the binder mixtures was at or close to 1.65:1. In calculating these quantities, it was assumed that all reactions producing polyols 1-5 or the oligomers of polyol 1 had proceeded to completion. This approach resulted in adding different proportions of PAA which caused variations in the pH of different binder systems. In most cases, calculated quantities of water were then added so that these compositions had a final water content of 69.1%, or the percent dry solids (DS) of these compositions was 30.9%. Sodium hypophosphite was typically added as a catalyst at fairly constant concentrations relative to the amount of dry solids incorporated in various binder compositions.

EXAMPLES

Descriptions of the experimental methods used to prepare polyols 1-5 and oligomers of polyols 1 and 2 used as binder components are described below. These examples are provided to illustrate various embodiments of the invention and are not intended to limit the scope of the invention in any way.

This example illustrates a method for preparing Furan 2,5-Dicarboxylic Acid Dimethyl Ester (FDME).

Furan 2,5-dicarboxylic acid (FDCA; 100.09 g; 0.641 mole) was added to a round bottomed flask containing sulfuric acid (5.46 mL; 0.102 mole) and methanol (1300 mL; 32.09 mole). The mixture was refluxed for 30 hours with magnetic stirring. This cooled mixture was passed through a course fritted filter to obtain an off-white precipitate and an orange filtrate. The precipitate was dissolve into 20% ethyl acetate in acetonitrile (700 mL) and neutralized with pre-washed Amberlyst® A-21 resin (300 mL) to remove non-reacted FDCA. The resin was removed by filtration and solvent was removed in a rotary evaporator and vacuum oven. The resulting off-white solid (87.94 g) was 99% pure by NMR spectroscopy. The orange filtrate was then neutralized by the same resin and treated by the same process. The resulting orange/brown product (24.00 g) was also 99% pure by proton NMR spectroscopy. The combined products corresponded to a combined yield of 94.8%.

Three exemplary methods for preparing polyol 1 are illustrated below.
Method 1

Furan 2,5-dimethyl ester (FDME; 31.90 g; 0.173 mole) was added to a round bottomed flask containing diethanolamine (56.50 g; 0.537 mole), sodium methoxide (1.87 g; 0.035 mole), and methanol (100 mL). The mixture was stirred for 1 hour and 10 minutes with magnetic stirring. After stirring, the mixture was purified by use of Amberlite® IR-120 resin (150 mL; 1.25 eq). The mixture was then filtered through a course fritted filter and solvent was removed by rotary evaporation followed by distillation. Proton NMR spectroscopy of product revealed 82.6% FDCA bisamide with a balance of the mixed FDCA amide/methyl ester. This product was isolated in a yield of 91.2%.
Method 2

Furan 2,5-dimethyl ester (FDME; 5.02 g; 0.027 mole) was added to a round bottomed flask containing diethanolamine (6.48 g; 0.062 mole), sodium methoxide (0.29 g; 0.005 mole), and methanol (10 mL). The mixture was refluxed for two hours with magnetic stirring. After reflux, the methanol was removed by short path distillation at 90° C. followed by use of a stream of argon to assist removal. After 2.5 hours the temperature was raised to 125° C. and the reaction proceeded for 4 hours. The mixture was dissolved into isopropyl alcohol and purified by use of Amberlite® IR-120 resin (18 mL; 1.5 eq). The mixture was then filtered through a course fritted filter and solvent was removed by rotary evaporation followed by distillation. NMR spectroscopy of this product revealed a composition 75 mole percent FDCA bisamide of diethanolamine and 25 mole percent mixed FDCA mixed amide/methyl ester.
Method 3

Furan 2,5-dimethyl ester (FDME; 20.07 g; 0.109 mole) was added to a round bottomed flask containing diethanolamine (33.92 g; 0.323 mole), sodium methoxide (1.98 g; 0.037 mole), and methanol (40 mL). The mixture was refluxed for 1 hour with magnetic stirring. After reflux, the methanol was removed by short path distillation at 125° C. followed by use of a stream of argon to assist removal. After two hours at 125° C., 2-(methylamino)ethanol (2 mL; 0.025 mole) was added and the reaction was continued for 3.5 hours. The mixture was dissolved in isopropyl alcohol and purified by use of Amberlite® IR-120 resin (131 mL; 1.5 eq). The mixture was then filtered through a course fritted filter and solvent was removed by rotary evaporation followed by distillation. NMR spectroscopy of product revealed (on a mole basis) 71.4% FDCA bisamide of diethanolamine, 10% FDCA mixed bisamide of diethanolamine and 2-(methylamino)ethanol, and 18% mixed FDCA amide/methyl ester.

An example of a method for preparing polyol 2 is shown below.

Furan 2,5-dimethyl ester (FDME; 15.00 g; 0.081 mole) was added to a round bottomed flask containing 2-(methylamino)ethanol (12.96 g; 0.173 mole), sodium methoxide (2.36 g; 0.044 mole), and methanol (75 mL). The mixture was stirred by magnetic stirrer for 10 minutes to dissolve the FDME and the flask was attached to a short path distillation apparatus and heated to 100° C. for two hours. The resulting mixture was dissolved into warm acetonitrile and stirred into pre-washed Amberlite® IR-120 resin (30 mL) until pH was neutral. The resin was removed by filtration and solvent was removed by rotary evaporation. Proton NMR spectroscopy indicated the desired structure and the product (21.87 grams) was obtained in 99% yield.

Method for Preparing Polyol 3

Furan 2,5-dimethyl ester (FDME; 5.01 g; 0.027 mole) was added to a round bottomed flask containing triethanolamine (7.28 g; 0.049 mole) and boron trifluoride diethyl etherate (1.70 mL; 0.014 mole). The mixture was heated with magnetic stirring to 120° C. for two hours. IR spectroscopy revealed an ester peak at 1722 cm$^{-1}$ and proton NMR spectroscopy revealed the expected presence of esterified methylene groups at 4.3-4.7 ppm.

Method for Preparing Polyol 4

Furan 2,5-dimethyl ester (FDME; 5.17 g; 0.028 mole) was added to a round bottomed flask containing tris(hydroxymethyl)aminomethane (Tris; 9.12 g; 0.075 mole), sodium methoxide (0.30 g; 0.006 mole), and methanol (40 mL) and the mixture was heated to 40° C. for 1 hour with magnetic stirring. More methanol (60 mL) was added to the mixture which was then filtered through a course fritted filter. The precipitate was rinsed with two 50 mL portions of methanol and the solid was then dried in a vacuum oven. The resulting solid was obtained in a yield of 90.4%.

Three Methods for preparing polyol 5 are exemplified below.
Method 1

Furan 2,5-dimethyl ester (FDME; 5.01 g; 0.027 mole) was added to a round bottomed flask containing glycerin (4.96 g; 0.054 mole) and boron trifluoride diethyl etherate (1.70 mL; 0.014 mole). The mixture was heated with magnetic stirring to 120° C. for 4.5 hours and the product was used without removal of excess glycerin.
Method 2

Furan 2,5-dicarboxylic acid (7.00 g; 0.045 mole) was added to a round bottomed flask containing glycerin (77.01 g; 0.836 mole). A short path distillation apparatus was attached and the mixture was heated to 150° C. with magnetic stirring for 30 minutes. The mixture was then heated to 200° C. at a vacuum of 0.4 mm Hg for 6 hours. The glycerin was then removed by distillation to produce the product in a yield of 90.8%.

Method 3

Furan 2,5-dicarboxylic acid (5.00 g; 0.032 mole) was added to a round bottomed flask containing glycerol (6.69 g; 0.073 mole), sodium hypophosphite (1.00 g), and water (1 mL). The mixture was heated to 250° C. with magnetic stirring for 1 hour and an argon stream was passed thought the apparatus for 50 minutes. IR spectra on the resulting product revealed a large hydroxyl peak with a significant ester peak and the product was produced without further purification.

The general process for preparing oligomers according to one aspect of the invention is exemplified below.

Oligomers of polyol 1 and FDCA and malic acid were prepared by heating various ratios of polyol 1 and FDCA under different sets of conditions while removing water of esterification to drive the esterification reactions to near completion. Infrared spectroscopy (IR) was used to monitor the relative completion of esterification reactions based on monitoring the carbonyl groups of the carboxylic acid. However, given the small differences between the frequencies of carboxylic acids and esters, it was not possible to detect small concentrations of unreacted carboxylic acid groups in the presence of major quantities of ester functionality. The presence of residual FDCA or malic acid groups was primarily indicated by pH measurements.

Three Methods for preparing an oligomer of polyol 1 and FDCA are exemplified below.

Method 1

This example describes the preparation of FDCA:polyol 1 oligomer with a 0.6:1 mole ratio and can be adjusted for preparing this type oligomer with other ratios of these two components. Polyol 1 (10.01 g; 0.032 mole) was added to a round bottomed flask containing furan 2,5-dicarboxylic acid (FDCA; 2.97 g; 0.019 mole), sodium hypophosphite (0.97 g; 7.5% of total weight), and water (2 mL). The mixture was heated to 150° C. for 15 minutes with magnetic stirring. The mixture was then heated to 175° C. while passing an argon stream through the head space of reaction apparatus for 25 minutes. The IR spectrum of the resulting hygroscopic solid supported the structure of the desired product based on the presence of both amide and ester peaks at 1610 cm$^{-1}$ and 1723 cm$^{-1}$, respectively.

Method 2

This example is for making FDCA:polyol 1 oligomer (0.7:1 mole ratio) and can be adjusted for making other ratios of the two components. Polyol 1 (7.62 g; 0.023 mole) was added to a round bottomed flask containing furan 2,5-dicarboxylic acid (FDCA; 2.65 g; 0.017 mole), sodium hypophosphite (0.77 g; 7.5% of total weight), and water (2 mL). The mixture was heated to 100° C. for 10 minutes with mechanical stirring. The temperature was then raised to 150° C. for 25 minutes and then to 175° C. for 40 minutes. The temperature was then finally raised to 190° C. for 20 minutes before heat was removed. The IR spectrum revealed an ester peak at 1720 cm$^{-1}$ and amide peak at 1610 cm$^{-1}$. Proton NMR spectroscopy also supported the desired reaction product.

Method 3

This example describes the preparation of FDCA:polyol 1 oligomer with a 0.9:1 mole ratio and can be adjusted for preparing this type oligomer with other ratios of these two components. Polyol 1 (12.32 g; 0.037 mole) was added to a round bottomed flask containing furan 2,5-dicarboxylic acid (FDCA; 5.21 g; 0.033 mole), sodium hypophosphite (0.12 g), and water (9 mL). The mixture was heated to 150° C. for 1 hour and 5 minutes with magnetic stirring and an argon stream through the head space of reaction apparatus. The IR spectrum of the resulting hygroscopic solid supported the structure of the desired product based on the presence of both amide and ester peaks at 1610 cm$^{-1}$ and 1723 cm$^{-1}$, respectively This example illustrates a method for preparing an oligomer of Malic Acid and polyol 1

This example describes the preparation of Malic Acid:polyol 1 oligomer (1:1 mole ratio) and can be adjusted for preparing other ratios of the two components. Polyol 1 (10.00 g; 0.030 mole) was added to a round bottomed flask containing malic acid (4.06 g; 0.030 mole), sodium hypophosphite (1.05 g; 7.5% of total weight), and water (2 mL). The mixture was heated to 150° C. for 10 minutes with magnetic stirring. The mixture was then heated to 175° C. while passing an argon stream through the reaction apparatus for 30 minutes. The IR spectrum of the hygroscopic solid supported its structure by the presence of amide and ester peaks at 1620 cm$^{-1}$ and 1721 cm$^{-1}$, respectively.

This example illustrates a method for preparing an oligomer of Malic Acid and Polyol 2

Polyol 2 (5.96 g; 0.022 mole) was added to a round bottomed flask containing malic acid (1.51 g; 0.011 mole), sodium hypophosphite (0.06 g; 0.80% of total weight), and acetonitrile (2 mL). The mixture was heated to 150° C. for two hours and 20 minutes while passing an argon gas stream through the apparatus. The IR spectrum supported its structure by the presence of an amide peak at 1615 cm$^{-1}$ and ester peak at 1725 cm$^{-1}$. Proton NMR spectroscopy also supported the structure of this product.

Tables A-1 to A-8 provide the components used to prepare individual binders that were evaluated in stroke/cure tests listed in Table B-1a through B8. The components used to prepare binder mixtures labeled 2a through 5, a through z, AA through ZZ, and AAA through EEE are described in these tables.

TABLE A-1

Binder Compositions for Tables B-1a and B-1b[a]

| Mixture | Polyol | Grams Polyol | Mole OH | % wt PAA | Grams PAA Sol | Grams PAA | Moles Acid | Grams Sodium Hypophosphite |
|---|---|---|---|---|---|---|---|---|
| Mix 2a | Polyol 1 | 3.07 | 0.0372 | 25 | 17.89 | 4.473 | 0.0616 | 0.56 |
| Mix 2b | Polyol 1 | 3.07 | 0.0372 | 25 | 17.9 | 4.475 | 0.0616 | 0 |
| Mix 3 | Polyol 1 | 3.07 | 0.0372 | 0 | 0 | 0.000 | 0.0000 | 0 |
| Mix 4 | Polyol 5 | 3.08 | 0.0304 | 25 | 17.9 | 4.475 | 0.0616 | 0.56 |
| Mix 5 | Polyol 4 | 2.25 | 0.0373 | 25 | 17.9 | 4.475 | 0.0616 | 0.56 |
| Mix 6 | Oligomer FDCA:Polyol 1 (1:1) | 4.2 | 0.0187 | 35 | 6.4 | 2.240 | 0.0309 | 0.25 |

TABLE A-1-continued

Binder Compositions for Tables B-1a and B-1b[a]

| Mixture | Moles Sodium Hypophosphite | % wt Sodium Hypophosphite wrt DS | Grams Water | Total Grams | Total Grams DS | % DS | % wt PAA | Acid to OH Ratio |
|---|---|---|---|---|---|---|---|---|
| Mix 2a | 0.0064 | 6.91 | 4.69 | 26.21 | 8.10 | 30.9 | 17.1 | 1.66 |
| Mix 2b | 0.0000 | 0.00 | 4.69 | 25.66 | 7.55 | 29.4 | 17.4 | 1.66 |
| Mix 3 | 0.0000 | 0.00 | 9.94 | 13.01 | 3.07 | 23.6 | 0.0 | 0.00 |
| Mix 4 | 0.0064 | 6.90 | 4.68 | 26.22 | 8.12 | 30.9 | 17.1 | 2.03 |
| Mix 5 | 0.0064 | 7.69 | 2.87 | 23.58 | 7.29 | 30.9 | 19.0 | 1.65 |
| Mix 6 | 0.0028 | 3.74 | 18.15 | 29.00 | 6.69 | 23.1 | 7.7 | 1.65 |

[a] 100,000 Mw Polyacrylic Acid (PAA)
DS = Dry Solids
wrt = with respect to

TABLE A-2

Binder Composition for Table B-2[a]

| Mixture | Polyol | Grams Polyol | Mole OH | % wt PAA | Grams PAA Sol | Grams Water from PAA | Grams PAA | Grams Succinic Anhy | Moles Acid from Succinic Acid | Moles Acid |
|---|---|---|---|---|---|---|---|---|---|---|
| Mix A | Oligomer FDCA:Polyol 1 (1:1) + Polyol 4 (9% wt wrt Polyol) | 1.23 | 0.0115 | 35 | 1.10 | 0.717 | 0.386 | 0.000 | 0.000 | 0.0053 |
| Mix B | Polyol 5[b] | 2.56 | 0.0372 | 35 | 12.79 | 8.314 | 4.477 | 0.000 | 0.000 | 0.0617 |
| Mix E | Oligomer FDCA:Polyol (0.9:1) | 2.10 | 0.0139 | 35 | 3.21 | 2.087 | 1.124 | 0.000 | 0.000 | 0.0155 |
| Mix G | Oligomer FDCA:Polyol 1 (0.9:1) | 2.10 | 0.0139 | 35 | 1.63 | 1.060 | 0.571 | 0.380 | 0.008 | 0.0155 |

| Mixture | Grams Sodium Hypophosphite | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|---|
| Mix A | 0.043 | 0.0005 | 2.59 | 4.75 | 5.467 | 7.13 | 1.66 | 23.3 | 5.4 | 0.46 |
| Mix B | 0.15 | 0.0017 | 2.09 | 11.9 | 20.214 | 27.40 | 7.19 | 26.2 | 16.3 | 1.66 |
| Mix E | 0.12 | 0.0014 | 3.59 | 9.1 | 11.187 | 14.53 | 3.34 | 23.0 | 7.7 | 1.11 |
| Mix G | 0.12 | 0.0014 | 3.78 | 9.22 | 10.280 | 13.45 | 3.17 | 23.6 | 4.2 | 1.11 |

[a] 100,000 Mw Polyacrylic Acid (PAA)
[b] FDCA + Glycerin (1:2.25 mole ratio) with hypophosphite catalyst and no removal of excess glycerin.
DS = Dry Solids
wrt = with respect to

TABLE A-3

Binder Compositions for Table B-3[a]

| Mixture | Polyol | Grams Polyol | Mole OH | % wt PAA | Grams PAA Sol | Grams Water from PAA | Grams PAA | Moles Acid | Grams Sodium Hypophosphite |
|---|---|---|---|---|---|---|---|---|---|
| Mix H | Oligomer FDCA:Polyol 1 (0.9:1) | 2.1 | 0.0139 | 35 | 4.75 | 3.088 | 1.663 | 0.0229 | 0.12 |
| Mix I | Oligomer FDCA:Polyol 1 (.9:1) + 5% wt Polyol 4 | 2.1 | 0.0138 | 35 | 4.72 | 3.068 | 1.652 | 0.0228 | 0.12 |
| Mix J | Oligomer FDCA:Polyol 1 (0.7:1) | 3.17 | 0.0278 | 35 | 9.51 | 6.182 | 3.329 | 0.0458 | 0.31 |
| Mix K | Oligomer FDCA Comp 1 (0.8:1) | 3.41 | 0.0278 | 35 | 9.52 | 6.188 | 3.332 | 0.0459 | 0.34 |
| Mix L | Oligomer FDCA:Polyol 1 (1:0.866) | 2.86 | 0.0139 | 35 | 4.76 | 3.094 | 1.666 | 0.0229 | 0.32 |

| Mixture | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|
| Mix H | 0.0014 | 3.09 | 5.6 | 8.688 | 12.57 | 3.88 | 30.9 | 13.2 | 1.65 |
| Mix I | 0.0014 | 3.10 | 5.6 | 8.668 | 12.54 | 3.87 | 30.9 | 13.2 | 1.65 |

TABLE A-3-continued

Binder Compositions for Table B-3[a]

| Mixture | | | | | | | | | |
|---|---|---|---|---|---|---|---|---|---|
| Mix J | 0.0035 | 4.55 | 9.045 | 15.227 | 22.04 | 6.81 | 30.9 | 15.1 | 1.65 |
| Mix K | 0.0039 | 4.80 | 9.65 | 15.838 | 22.92 | 7.08 | 30.9 | 14.5 | 1.65 |
| Mix L | 0.0036 | 6.60 | 7.75 | 10.844 | 15.69 | 4.85 | 30.9 | 10.6 | 1.65 |

[a]100,000 Mw Polyacrylic Acid (PAA)
DS = Dry Solids
Wrt = with respect to

TABLE A-4

Binder Compositions for Table B-4[a]

| Mixture | Polyol | Grams Polyol | Mole OH | % wt PAA | Grams PAA Sol | Grams Water from PAA | Grams PAA | Grams Succinic Acid | Moles Acid from Succinic Acid | Moles Acid |
|---|---|---|---|---|---|---|---|---|---|---|
| Mix M | Oligomer FDCA:Polyol 1 (0.9:1) | 1.05 | 0.0070 | 35 | 0 | 0.000 | 0.000 | 0.460 | 0.0078 | 0.0078 |
| Mix I | Oligomer FDCA:Polyol 1 (.9:1) + 5% wt Polyol 4 | 2.1 | 0.0138 | 35 | 4.72 | 3.068 | 1.652 | 0.000 | 0.000 | 0.0228 |
| Mix J | Oligomer FDCA:Polyol 1 (0.7:1) | 3.17 | 0.0278 | 35 | 9.51 | 6.182 | 3.329 | 0.000 | 0.000 | 0.0458 |
| Mix O | Polyol 5[b] | 1.38 | 0.0372 | 35 | 12.78 | 8.307 | 4.473 | 0.000 | 0.000 | 0.0616 |
| Mix E-1 | Oligomer FDCA:Polyol 1 (0.9:1) | 0.53 | 0.0035 | 35 | 0.8 | 0.520 | 0.280 | 0.000 | 0.000 | 0.0039 |
| Mix E-2 | Oligomer FDCA:Polyol 1 (0.9:1) | 0.53 | 0.0035 | 35 | 0.8 | 0.520 | 0.280 | 0.000 | 0.000 | 0.0039 |

| Mixture | Grams Sodium Hypophosphite | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|---|
| Mix M | 0.06 | 0.0007 | 3.82 | 3.5 | 3.500 | 4.61 | 1.57 | 34.1 | 0.0 | 1.12 |
| Mix I | 0.12 | 0.0014 | 3.10 | 5.6 | 8.668 | 12.54 | 3.87 | 30.9 | 13.2 | 1.65 |
| Mix J | 0.31 | 0.0035 | 4.55 | 9.045 | 15.227 | 22.04 | 6.81 | 30.9 | 15.1 | 1.65 |
| Mix O | 0.59 | 0.0067 | 9.16 | 6.1 | 14.407 | 20.85 | 6.44 | 30.9 | 21.5 | 1.66 |
| Mix E-1 | 0.03 | 0.0003 | 3.57 | 1.35 | 1.870 | 2.71 | 0.84 | 31.0 | 10.3 | 1.11 |
| Mix E-2 | 0.08 | 0.0009 | 8.9888 | 1.45 | 1.970 | 2.86 | 0.89 | 31.1 | 9.8 | 1.11 |

[a]100,000 Mw Polyacrylic Acid (PAA)
[b]FDME + Glycerin (1:8 mole ratio) with BF3 catalyst and no removal of excess glycerin.
DS = Dry Solids
wrt = with respect to

TABLE A-5

Binder Compositions for Table B-5[a]

| Mixture | Polyol | Grams Polyol | Mole OH | % wt PAA | Grams PAA Sol | Grams Water from PAA | Grams PAA | Grams Succinic or Malic Acid | Moles Acid from Succinic or Malic Acid | Moles Acid |
|---|---|---|---|---|---|---|---|---|---|---|
| Mix P | Polyol 5[b] | 1.42 | 0.0187 | 35 | 6.39 | 4.154 | 2.237 | 0.000 | 0.0000 | 0.0308 |
| Mix Q | Polyol 3[c] | 2.29 | 0.0186 | 35 | 6.39 | 4.154 | 2.237 | 0.000 | 0.000 | 0.0308 |
| Mix R | Oligomer FDCA:Polyol 1 (0.6:1) | 1.03 | 0.0062 | 35 | 2.13 | 1.385 | 0.746 | 0.000 | 0.000 | 0.0103 |
| Mix S | Oligomer FDCA:Polyol 1 (0.6:1)[d] | 1.03 | 0.0062 | 35 | 1.07 | 0.696 | 0.375 | 0.320 | 0.005 | 0.0106 |
| Mix T | Oligomer FDCA:Polyol 1 (0.6:1)[e] | 1.03 | 0.0062 | 35 | 0 | 0.000 | 0.000 | 1.390 | 0.010 | 0.0103 |
| Mix U | Polyol 1[e] | 1.1 | 0.0124 | 35 | 0 | 0.000 | 0.000 | 2.770 | 0.021 | 0.0205 |

| Mixture | Grams Sodium Hypophosphite | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|---|
| Mix P | 0.36 | 0.0041 | 8.96 | 4.83 | 8.984 | 13.00 | 4.02 | 30.9 | 17.2 | 1.65 |
| Mix Q | 0.45 | 0.0051 | 9.04 | 6.99 | 11.144 | 16.12 | 4.98 | 30.9 | 13.9 | 1.66 |
| Mix R | 0.18 | 0.0020 | 9.20 | 2.98 | 4.365 | 6.32 | 1.96 | 30.9 | 11.8 | 1.66 |
| Mix S | 0.17 | 0.0019 | 8.97 | 3.5 | 4.196 | 6.09 | 1.89 | 31.1 | 6.1 | 1.70 |

TABLE A-5-continued

Binder Compositions for Table B-5[a]

| | | | | | | | | | | |
|---|---|---|---|---|---|---|---|---|---|---|
| Mix T | 0.24 | 0.0027 | 9.02 | 5.95 | 5.950 | 8.61 | 2.66 | 30.9 | 0.0 | 1.66 |
| Mix U | 0.38 | 0.0043 | 8.9412 | 9.54 | 9.540 | 13.79 | 4.25 | 30.8 | 0.0 | 1.65 |

[a]100,000 Mw Polyacrylic Acid (PAA)
[b]FDME + Glycerin (1:2 mole ratio) with BF3 catalyst and no removal of excess glycerin.
[c]FDME + Triethanolamine (1:1.8 mole ratio) with BF3 catalyst and no removal of excess triethanolamine.
[d]Succinic Acid used for cure.
[e]Malic Acid used for cure.
DS = Dry Solids
wrt = with respect to

TABLE A-6

Binder Compositions for Table B-6[a]

| Mixture | Polyol | Grams Polyol | Mole OH | % wt PAA | Grams PAA Sol | Grams Water from PAA | Grams PAA | Grams Succinic Acid | Moles Acid from Succinic Acid | Moles Acid |
|---|---|---|---|---|---|---|---|---|---|---|
| Mix R | Oligomer FDCA:Polyol 1 (0.6:1) | 1.03 | 0.0062 | 35 | 2.13 | 1.385 | 0.746 | 0.000 | 0.000 | 0.0103 |
| Mix Q | Polyol 3[b] | 2.29 | 0.0186 | 35 | 6.39 | 4.154 | 2.237 | 0.000 | 0.000 | 0.0308 |
| Mix S | Oligomer FDCA:Polyol 1 (0.6:1) | 1.03 | 0.0062 | 35 | 1.07 | 0.696 | 0.375 | 0.320 | 0.005 | 0.0106 |
| Mix V | Polyol 3[b] | 1.53 | 0.0124 | 35 | 4.26 | 2.769 | 1.491 | 0.000 | 0.000 | 0.0205 |
| Mix W | Polyol 3[c] | 1.53 | 0.0124 | 35 | 4.26 | 2.769 | 1.491 | 0.000 | 0.000 | 0.0205 |
| Mix X | Polyol 5[d] | 0.94 | 0.0124 | 35 | 4.26 | 2.769 | 1.491 | 0.000 | 0.000 | 0.0205 |
| Mix Y | Polyol 5[e] | 0.94 | 0.0124 | 35 | 4.26 | 2.769 | 1.491 | 0.000 | 0.000 | 0.0205 |
| Mix Z | Oligomer FDCA:Polyol 1 (0.6:1) | 2.05 | 0.0124 | 35 | 4.26 | 2.769 | 1.491 | 0.000 | 0.000 | 0.0205 |
| Mix AA | Oligomer FDCA:Polyol 1 (0.7:1) | 2.31 | 0.0124 | 35 | 4.26 | 2.769 | 1.491 | 0.000 | 0.000 | 0.0205 |
| Mix BB | Polyol 3[f] | 1.13 | 0.0124 | 35 | 4.26 | 2.769 | 1.491 | 0.000 | 0.000 | 0.0205 |
| Mix CC | Malic Acid + Polyol 2 (1:2) | 1.59 | 0.0075 | 35 | 2.56 | 1.664 | 0.896 | 0.000 | 0.000 | 0.0123 |
| Mix DD | Polyol 1 | 1.11 | 0.0124 | 35 | 4.26 | 2.769 | 1.491 | 0.000 | 0.000 | 0.0205 |

| Mixture | Grams Sodium Hypophosphite | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|---|
| Mix R | 0.18 | 0.0020 | 9.20 | 2.98 | 4.365 | 6.32 | 1.96 | 30.9 | 11.8 | 1.66 |
| Mix Q | 0.45 | 0.0051 | 9.04 | 6.99 | 11.144 | 16.12 | 4.98 | 30.9 | 13.9 | 1.66 |
| Mix S | 0.17 | 0.0019 | 8.97 | 3.5 | 4.196 | 6.09 | 1.89 | 31.1 | 6.1 | 1.70 |
| Mix V | 0.3 | 0.0034 | 9.03 | 4.66 | 7.429 | 10.75 | 3.32 | 30.9 | 13.9 | 1.66 |
| Mix W | 0.3 | 0.0034 | 9.03 | 4.66 | 7.429 | 10.75 | 3.32 | 30.9 | 13.9 | 1.66 |
| Mix X | 0.24 | 0.0027 | 8.99 | 3.22 | 5.989 | 8.66 | 2.67 | 30.8 | 17.2 | 1.66 |
| Mix Y | 0.24 | 0.0027 | 8.99 | 3.22 | 5.989 | 8.66 | 2.67 | 30.8 | 17.2 | 1.66 |
| Mix Z | 0.35 | 0.0040 | 9.00 | 5.95 | 8.719 | 12.61 | 3.89 | 30.9 | 1.18 | 1.66 |
| Mix AA | 0.38 | 0.0043 | 9.09 | 6.6 | 9.369 | 13.55 | 4.18 | 30.9 | 11.0 | 1.66 |
| Mix BB | 0.26 | 0.0030 | 9.02 | 3.68 | 6.449 | 9.33 | 2.88 | 30.9 | 16.0 | 1.66 |
| Mix CC | 0.24 | 0.0027 | 8.80 | 4.43 | 6.094 | 8.82 | 2.73 | 30.9 | 10.2 | 1.65 |
| Mix DD | 0.26 | 0.0030 | 9.09 | 3.62 | 6.389 | 9.25 | 2.86 | 30.9 | 16.1 | 1.66 |

[a]100,000 Mw Polyacrylic Acid (PAA)
[b]FDME + Triethanolamine (1:1.8 mole ratio) with BF3 catalyst and no removal of excess triethanolamine.
[c]FDME + Triethanolamine (1:1.8 mole ratio) with BF3 catalyst, neutralized, and no removal of excess triethanolamine.
[d]FDME + Glycerin (1:2 mole ratio) with BF3 catalyst and no removal of excess glycerin.
[e]FDME + Glycerin (1:2 mole ratio) with BF3 catalyst, neutralized, and no removal of excess glycerin.
[f]FDME + Triethanolamine (1:2.2 mole ratio) with BF3 catalyst and no removal of excess triethanolamine.
DS = Dry Solids
wrt = with respect to

TABLE A-8

Binder Compositions for Table B-8[a]

| Mixture | Polyol | Grams Polyol | Mole OH | % wt PAA | Grams PAA Sol | Grams Water from PAA | Grams PAA | Moles Acid | Grams Sodium Hypophosphite |
|---|---|---|---|---|---|---|---|---|---|
| Mix YY | Polyol 1 | 1.10 | 0.0124 | 35 | 4.26 | 2.769 | 1.491 | 0.0205 | 0.26 |
| Mix ZZ | Polyol 1 | 1.10 | 0.0124 | 35 | 4.27 | 2.776 | 1.495 | 0.0206 | 0.08 |

TABLE A-8-continued

Binder Compositions for Table B-8[a]

| | | | | | | | | | |
|---|---|---|---|---|---|---|---|---|---|
| Mix AAA | Oligomer Malic Acid:Polyol 1 (1:1) | 1.48 | 0.0093 | 35 | 3.20 | 2.080 | 1.120 | 0.0154 | 0.26 |
| Mix BBB | Oligomer FDCA:Polyol 1 (0.6:1) | 0.86 | 0.0053 | 35 | 1.83 | 1.190 | 0.641 | 0.0088 | 0.15 |
| Mix CCC | Oligomer FDCA:Polyol 1 (0.6:1) | 0.86 | 0.0053 | 35 | 1.83 | 1.190 | 0.641 | 0.0088 | 0.15 |
| Mix DDD | Oligomer FDCA:Polyol 1 (0.6:1) | 1.00 | 0.0062 | 35 | 2.13 | 1.385 | 0.746 | 0.0103 | 0.17 |
| Mix EEE | Oligomer FDCA:Polyol 1 (0.6:1) | 1.66 | 0.0103 | 35 | 2.56 | 1.664 | 0.896 | 0.0123 | 0.26 |

| Mixture | Moles Sodium Hypophosphite | % wt Sodium Hypophosphite wrt DS | Grams Water | Total Grams of Water | Total Grams | Total Grams DS | % DS | % wt PAA | Acid to OH Ratio |
|---|---|---|---|---|---|---|---|---|---|
| Mix YY | 0.0030 | 9.12 | 3.59 | 6.359 | 9.21 | 2.85 | 31.0 | 16.2 | 1.66 |
| Mix ZZ | 0.0009 | 2.99 | 3.20 | 5.976 | 8.65 | 2.67 | 30.9 | 17.3 | 1.66 |
| Mix AAA | 0.0030 | 9.09 | 4.31 | 6.390 | 9.25 | 2.86 | 30.9 | 12.1 | 1.66 |
| Mix BBB | 0.0017 | 9.09 | 2.49 | 3.680 | 5.33 | 1.65 | 31.0 | 12.0 | 1.66 |
| Mix CCC | 0.0017 | 9.09 | 1.28 | 2.470 | 4.12 | 1.65 | 40.1 | 15.5 | 1.66 |
| Mix DDD | 0.0019 | 8.87 | 0.54 | 1.925 | 3.84 | 1.92 | 49.9 | 19.4 | 1.66 |
| Mix EEE | 0.0030 | 9.23 | 4.64 | 6.304 | 9.12 | 2.82 | 30.9 | 9.8 | 1.20 |

[a]100,000 Mw Polyacrylic Acid (PAA)
DS = Dry Solids
wrt = with respect to

Tables B-1a to B-8 provide the results of stroke/cure tests obtained on different days for mixtures of polyols and PAA specified in Tables A-1a to A-8. Tables B-1a through B-8 also provide additional experimental conditions.

TABLE B-1a

Stroke-Cure Test Results with FDCA-Based Polyols on 180 C. Hot Plate 1st Round[a]

| | Notation | | String Time[b] | Cure Time[b] | Solubility at Ambient | | % wt | |
|---|---|---|---|---|---|---|---|---|
| Composition | Run No. | Mixture | (sec) | (sec) | Temperature | Comments | PAA | % DS |
| Polyol 1 | 3 | 2a | 71 | 83 | Soluble | pH: 2-3<br>1.66 Acid to OH ratio<br>Catalyst: 6.91% Sodium Hypophosphite wrt DS | 17.1 | 30.9 |
| Polyol 1 | 4 | 2a | 73 | 84 | Soluble | pH: 2-3<br>1.66 Acid to OH ratio<br>Catalyst: 6.91% Sodium Hypophosphite wrt DS | 17.1 | 30.9 |
| Polyol 1 | 5 | 2b | 71 | 86 | Soluble | pH: 2-3<br>1.66 Acid to OH ratio<br>No Catalyst | 17.4 | 29.4 |
| Polyol 1 | 6 | 2b | 73 | 88 | Soluble | pH: 2-3<br>1.66 Acid to OH ratio<br>No Catalyst | 17.4 | 29.4 |
| Polyol 1 | 7 | 3 | none | none | Soluble | No Catalyst: No PAA;<br>Did not solidify after cooling | 0 | 23.6 |
| Polyol 4 | 9 | 5 | 63 | 73 | Insoluble | pH: 2-3<br>1.65 Acid to OH ratio<br>Catalyst: 7.69% Sodium Hypophosphite wrt DS | 19 | 30.9 |
| Polyol 5[c] | 10 | 4 | 76 | 103 | Insoluble | pH: 1<br>2.03 Acid to OH ratio<br>Catalyst: 6.90% Sodium Hypophosphite wrt DS | 17.1 | 30.9 |

[a]1. Mixtures 4 and 5 required pre-heating (65-75 C) to solubilize. 2. All pH measurements were performed with colorpHast ® paper 3. Unless stated, all cured binders solidified when cooled. 4. In calculating Acid/OH ratio, assumed that all reactions went to completion.
[b]Performed by stroke/cure test while allowing mixture to pre-volatilize approximately 20 seconds before stroking started.
[c]FDCA + Glycerin (1:4 mole ratio) with no catalyst and excess glycerin was removed by distillation.

wrt = with respect to

TABLE B-1b

Stroke-Cure Test Results with FDCA-Based Polyols on 180 C. Hot Plate 2nd Round[a]

| Composition | Notation Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 4 | 3 | 5 | 52 | 64 | Insoluble | pH: 2-3<br>1.65 Acid to OH ratio<br>Catalyst: 7.69% Sodium Hypophosphite wrt DS | 19 | 30.9 |
| Polyol 4 | 4 | 5 | 55 | 68 | Insoluble | pH: 2-3<br>1.65 Acid to OH ratio<br>Catalyst: 7.69% Sodium Hypophosphite wrt DS | 19 | 30.9 |
| Polyol 5[c] | 5 | 4 | 65 | 78 | Insoluble | pH: 1, tacky solid when cooled<br>2.03 Acid to OH ratio<br>Catalyst: 6.90% Sodium Hypophosphite wrt DS | 17.1 | 30.9 |
| Polyol 5[c] | 6 | 4 | 68 | 82 | Insoluble | pH: 1, tacky solid when cooled<br>2.03 Acid to OH ratio<br>Catalyst: 6.90% Sodium Hypophosphite wrt DS | 17.1 | 30.9 |
| Oligomer FDCA:Polyol 1 (1:1) | 7 | 6 | 66 | 76 | Insoluble | pH: 2.5-3<br>1.65 Acid to OH ratio<br>Catalyst: 6.90% Sodium Hypophosphite wrt DS | 7.7 | 23.1 |
| Oligomer FDCA:Polyol 1 (1:1) | 8 | 6 | 68 | 75 | Insoluble | pH: 2.5-3<br>1.65 Acid to OH ratio<br>Catalyst: 6.90% Sodium Hypophosphite wrt DS | 7.7 | 23.1 |

[a]1. All mixtures required pre-heating to solubilize. 2. All pH measurements were performed with colorpHast ® paper. 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 20 seconds before stroking started.
[c]FDCA + Glycerin (1:4 mole ratio) with no catalyst and excess glycerin was removed by distillation.
wrt = with respect to

TABLE B-2

Stroke-Cure Test Results with FDCA-Based Polyols on 180 C. Hot Plate 3rd Round[a]

| Composition | Notation Run No. | Notation Mixture | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.9:1) | 3 | G | 70 | 90 | Insoluble | pH: 2-3<br>Acid was 50:50 PAA:Succinic Anhydride<br>Catalyst: 3.78% Sodium Hypophosphite wrt DS | 4.2 | 23.6 |
| Oligomer FDCA:Polyol 1 (0.9:1) | 4 | G | 75 | 92 | Insoluble | pH: 2-3<br>Acid was 50:50 PAA:Succinic Anhydride<br>Catalyst: 3.78% Sodium Hypophosphite wrt DS | 4.2 | 23.6 |
| Oligomer FDCA:Polyol 1 (1:1) + Polyol 4 (9% wt wrt Polyol) | 5 | A | 50 | 62 | Insoluble | pH: 3<br>.46 Acid to OH ratio<br>Catalyst: 2.59% Sodium Hypophosphite wrt DS | 5.4 | 23.3 |
| Oligomer FDCA:Polyol 1 (1:1) + Polyol 4 (9% wt wrt Polyol) | 6 | A | 48 | 60 | Insoluble | pH: 3<br>.46 Acid to OH ratio<br>Catalyst: 2.59% Sodium Hypophosphite wrt DS | 5.4 | 23.3 |
| Oligomer FDCA:Polyol 1 (0.9:1) | 7 | E | 45 | 65 | Insoluble | pH: 2.5-3<br>1.11 Acid to OH ratio<br>Catalyst: 3.59% Sodium Hypophosphite wrt DS | 7.7 | 23.0 |
| Oligomer FDCA:Polyol 1 (0.9:1) | 8 | E | 45 | 66 | Insoluble | pH: 2.5-3<br>1.11 Acid to OH ratio<br>Catalyst: 3.59% Sodium Hypophosphite wrt DS | 7.7 | 23.0 |
| Polyol 5[c] | 9 | B | 70 | 90 | Insoluble | pH: 1-2<br>1.66 Acid to OH ratio<br>Catalyst: 2.09% Sodium Hypophosphite wrt DS | 16.3 | 26.2 |
| Polyol 5[c] | 10 | B | 64 | 80 | Insoluble | pH: 1-2<br>1.66 Acid to OH ratio<br>Catalyst: 2.09% Sodium Hypophosphite wrt DS | 16.3 | 26.2 |

[a]1. All mixtures required pre-heating to solubilize. 2. All pH measurements were performed with colorpHast ® paper 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 20 seconds before stroking started.
[c]FDCA + Glycerin (1:2.25 mole ratio) with hypophosphite catalyst and no removal of excess glycerin.
wrt = with respect to

TABLE B-3

Stroke-Cure Test Results with FDCA-Based Polyols on 180° C. Hot Plate 4th Round[a]

| Composition | Run No. | Mixture Notation | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.7:1) | 3 | J | 60 | 77 | Soluble | pH: 2-3<br>1.65 Acid to OH ratio<br>Catalyst: 4.55% Sodium Hypophosphite wrt DS | 15.1 | 30.9 |
| Oligomer FDCA:Polyol 1 (0.7:1) | 4 | J | 65 | 84 | Soluble | pH: 2-3<br>1.65 Acid to OH ratio<br>Catalyst: 4.55% Sodium Hypophosphite wrt DS | 15.1 | 30.9 |
| Oligomer (FDCA:Polyol 1; 0.8:1) | 5 | K | 65 | 85 | Soluble | pH: 2-3<br>1.65 Acid to OH ratio<br>Catalyst: 4.80% Sodium Hypophosphite wrt DS | 14.5 | 30.9 |
| Oligomer FDCA:Polyol 1 (0.8:1) | 6 | K | 60 | 80 | Soluble | pH: 2-3<br>1.65 Acid to OH ratio<br>Catalyst: 4.80% Sodium Hypophosphite wrt DS | 14.5 | 30.9 |
| Oligomer FDCA:Polyol 1 (0.9:1) | 7 | H | 70 | 85 | Insoluble | pH: 2-3<br>1.65 Acid to OH ratio<br>Catalyst: 3.09% Sodium Hypophosphite wrt DS | 13.2 | 30.9 |
| Oligomer FDCA:Polyol 1 (0.9:1) | 8 | H | 60 | 75 | Insoluble | pH: 2-3<br>1.65 Acid to OH ratio<br>Catalyst: 3.09% Sodium Hypophosphite wrt DS | 13.2 | 30.9 |
| Oligomer FDCA:Polyol 1 (1:0.866) | 9 | L | 70 | 100 | Soluble | pH: 2-3<br>1.65 Acid to OH ratio<br>Catalyst: 6.60% Sodium Hypophosphite wrt DS | 10.6 | 30.9 |
| Oligomer FDCA:Polyol 1 (1:0.866) | 10 | L | 67 | 90 | Soluble | pH: 2-3<br>1.65 Acid to OH ratio<br>Catalyst: 6.60% Sodium Hypophosphite wrt DS | 10.6 | 30.9 |
| Oligomer FDCA:Polyol 1 (0.9:1) + 5% wt Polyol 4 | 11 | I | 65 | 75 | Insoluble | pH: 2-3<br>1.65 Acid to OH ratio<br>Catalyst: 3.10% Sodium Hypophosphite wrt DS | 13.2 | 30.9 |
| Oligomer FDCA:Polyol 1 (0.9:1) + 5% wt Polyol 4 | 12 | I | 62 | 74 | Insoluble | pH: 2-3<br>1.65 Acid to OH ratio<br>Catalyst: 3.10% Sodium Hypophosphite wrt DS | 13.2 | 30.9 |

[a]1. Mixtures H and I required pre-heating to solubilize. 2. All pH measurements were performed with colorpHast ® paper 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 30 seconds before stroking started.
wrt = with respect to

TABLE B-4

Stroke-Cure Test Results with FDCA-Based Polyols on 180° C. Hot Plate 5th Round[a]

| Composition | Run No. | Mixture Notation | String Time[b] (sec) | Cure Time[b] (sec) |  | Comments | % PAA | % DS |
|---|---|---|---|---|---|---|---|---|
| Oligomer FDCA:Polyol 1 (0.9:1) | 3 | M | — | No Cure | Insoluble | pH: 2-3<br>1.12 Acid to OH ratio<br>Catalyst: 3.82% Sodium Hypophosphite wrt DS<br>100% Acid is Succinic Acid | 0 | 34.1 |
| Oligomer FDCA:Polyol 1 (0.9:1) | 4 | M | — | No Cure | Insoluble | pH: 2-3<br>1.12 Acid to OH ratio<br>Catalyst: 3.82% Sodium Hypophosphite wrt DS<br>100% Acid is Succinic Acid | 0 | 34.1 |
| Oligomer FDCA:Polyol 1 (0.9:1) | 5 | E-1 | 57 | 67 | Insoluble | pH: 2-3<br>1.11 Acid to OH ratio<br>Catalyst: 3.57% Sodium Hypophosphite wrt DS | 10.3 | 31.0 |
| Oligomer FDCA:Polyol 1 (0.9:1) | 6 | E-1 | 58 | 70 | Insoluble | pH: 2-3<br>1.11 Acid to OH ratio<br>Catalyst: 3.57% Sodium Hypophosphite wrt DS | 10.3 | 31.0 |
| Oligomer FDCA:Polyol 1 (0.9:1) | 7 | E-2 | 50 | 64 | Insoluble | pH: 2-3<br>1.11 Acid to OH ratio<br>Catalyst: 8.99% Sodium Hypophosphite wrt DS | 9.8 | 31.1 |
| Oligomer FDCA:Polyol 1 (0.9:1) | 8 | E-2 | 50 | 62 | Insoluble | pH: 2-3<br>1.11 Acid to OH ratio<br>Catalyst: 8.99% Sodium Hypophosphite wrt DS | 9.8 | 31.1 |
| Polyol 5[c] | 9 | O | 55 | 72 | Soluble | pH: 1-2<br>1.66 Acid to OH ratio<br>Catalyst: 9.16% Sodium Hypophosphite wrt DS | 21.5 | 30.9 |

TABLE B-4-continued

Stroke-Cure Test Results with FDCA-Based Polyols on 180° C. Hot Plate 5th Round[a]

| Composition | Notation Run No. | Notation Mixture | String Time[b] (sec) | Cure Time[b] (sec) | | Comments | % PAA | % DS |
|---|---|---|---|---|---|---|---|---|
| Polyol 5[c] | 10 | O | 60 | 65 | Soluble | pH: 1-2<br>1.66 Acid to OH ratio<br>Catalyst: 9.16% Sodium Hypophosphite wrt DS | 21.5 | 30.9 |
| Oligomer FDCA:Polyol 1 (0.9:1) + 5% wt Polyol 4 | 11 | I | 45 | 55 | Insoluble | pH: 2-3<br>1.65 Acid to OH ratio<br>Catalyst: 3.10% Sodium Hypophosphite wrt DS | 13.2 | 30.9 |
| Oligomer FDCA:Polyol 1 (0.9:1) + 5% wt Polyol 4 | 12 | I | 48 | 59 | Insoluble | pH: 2-3<br>1.65 Acid to OH ratio<br>Catalyst: 3.10% Sodium Hypophosphite wrt DS | 13.2 | 30.9 |
| Oligomer FDCA:Polyol 1 (0.7:1) | 13 | J | 45 | 56 | Soluble | pH: 2-3<br>1.65 Acid to OH ratio<br>Catalyst: 4.55% Sodium Hypophosphite wrt DS | 15.1 | 30.9 |
| Oligomer FDCA:Polyol 1 (0.7:1) | 14 | J | 47 | 57 | Soluble | pH: 2-3<br>1.65 Acid to OH ratio<br>Catalyst: 4.55% Sodium Hypophosphite wrt DS | 15.1 | 30.9 |

[a]1. All mixtures required pre-heating to solubilize except for mixtures J and O. 2. All pH measurements were performed with colorpHast ® paper 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 10 seconds before stroking started.
[c]FDME + Glycerin (1:8 mole ratio) with BF3 catalyst and no removal of excess glycerin.
wrt = with respect to

TABLE B-5

Stroke-Cure Test Results with FDCA-Based Polyols on 180° C. Hot Plate 6th Round[a]

| Composition | Notation Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 5[c] | 3 | P | 55 | 65 | Soluble | pH: 1.08<br>1.65 Acid to OH ratio<br>Catalyst: 8.96% Sodium Hypophosphite wrt DS | 17.2 | 30.9 |
| Polyol 5[c] | 4 | P | 50 | 62 | Soluble | pH: 1.08<br>1.65 Acid to OH ratio<br>Catalyst: 8.96% Sodium Hypophosphite wrt DS | 17.2 | 30.9 |
| Polyol 3[d] | 5 | Q | 40 | 55 | Soluble | pH: 3.36<br>1.66 Acid to OH ratio<br>Catalyst: 9.04% Sodium Hypophosphite wrt DS | 13.9 | 30.9 |
| Polyol 3[d] | 6 | Q | 42 | 58 | Soluble | pH: 3.36<br>1.66 Acid to OH ratio<br>Catalyst: 9.04% Sodium Hypophosphite wrt DS | 13.9 | 30.9 |
| Oligomer FDCA:Polyol 1 (0.6:1) | 7 | R | 40 | 56 | Soluble | pH: 2.53<br>1.66 Acid to OH ratio<br>Catalyst: 9.20% Sodium Hypophosphite wrt DS | 11.8 | 30.9 |
| Oligomer FDCA:Polyol 1 (0.6:1) | 8 | R | 41 | 58 | Soluble | pH: 2.53<br>1.66 Acid to OH ratio<br>Catalyst: 9.20% Sodium Hypophosphite wrt DS | 11.8 | 30.9 |
| Oligomer FDCA:Polyol 1 (0.6:1) | 9 | S | 72 | 100 | Soluble | pH: 2.54<br>1.70 Acid to OH ratio<br>Catalyst: 8.97% Sodium Hypophosphite wrt DS<br>50% Succinic Acid | 6.1 | 31.1 |
| Oligomer FDCA:Polyol 1 (0.6:1) | 10 | S | 70 | 90 | Soluble | pH: 2.54<br>1.70 Acid to OH ratio<br>Catalyst: 8.97% Sodium Hypophosphite wrt DS<br>50% Succinic Acid | 6.1 | 31.1 |
| Oligomer FDCA:Polyol 1 (0.6:1) | 11 | T | None | 250 | Soluble | pH: 2.04<br>1.66 Acid to OH ratio<br>Catalyst: 9.02% Sodium Hypophosphite wrt DS<br>100% Malic Acid | 0 | 30.9 |
| Oligomer FDCA:Polyol 1 (0.6:1) | 12 | T | — | — | Soluble | pH: 2.04<br>1.66 Acid to OH ratio<br>Catalyst: 9.02% Sodium Hypophosphite wrt DS<br>100% Malic Acid | 0 | 30.9 |
| Polyol 1 | 13 | U | — | >120 | Soluble | pH: 1.54<br>1.65 Acid to OH ratio<br>Catalyst: 8.94% Sodium Hypophosphite wrt DS<br>100% Malic Acid | 0 | 30.8 |

TABLE B-5-continued

Stroke-Cure Test Results with FDCA-Based Polyols on 180° C. Hot Plate 6th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 1 | 14 | U | None | 185 | Soluble | pH: 1.54<br>1.65 Acid to OH ratio<br>Catalyst: 8.94% Sodium Hypophosphite wrt DS<br>100% Malic Acid | 0 | 30.8 |

[a]1. No mixtures required warming for solubilization but mixtures P and Q were cloudy. 2. All pH measurements were performed with a pH meter calibrated at pH 4 and 7. 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 10 seconds before stroking started.
[c]FDME + Glycerin (1:2 mole ratio) with BF3 catalyst and no removal of excess glycerin.
[d]FDME + Triethanolamine (1:1.8 mole ratio) with BF3 catalyst and no removal of excess triethanolamine.
wrt = with respect to

TABLE B-6

Stroke-Cure Test Results with FDCA-Based Polyols on 180° C. Hot Plate 7th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.6:1) | 3 | R | 50 | 60 | Soluble | pH: 2.53<br>1.66 Acid to OH ratio<br>Catalyst: 9.20% Sodium Hypophosphite wrt DS | 11.8 | 30.9 |
| Oligomer FDCA:Polyol 1 (0.6:1) | 4 | R | 42 | 53 | Soluble | pH: 2.53<br>1.66 Acid to OH ratio<br>Catalyst: 9.20% Sodium Hypophosphite wrt DS | 11.8 | 30.9 |
| Polyol 3[e] | 5 | Q | 39 | 50 | Soluble | pH: 3.36<br>1.66 Acid to OH ratio<br>Catalyst: 9.04% Sodium Hypophosphite wrt DS | 13.9 | 30.9 |
| Polyol 3[e] | 6 | Q | 42 | 55 | Soluble | pH: 3.36<br>1.66 Acid to OH ratio<br>Catalyst: 9.04% Sodium Hypophosphite wrt DS | 13.9 | 30.9 |
| Polyol 3[e] | 7 | V | 40 | 50 | Insoluble | pH: 3.56<br>1.66 Acid to OH ratio<br>Catalyst: 9.03% Sodium Hypophosphite wrt DS | 13.9 | 30.9 |
| Polyol 3[e] | 8 | V | 43 | 51 | Insoluble | pH: 3.56<br>1.66 Acid to OH ratio<br>Catalyst: 9.03% Sodium Hypophosphite wrt DS | 13.9 | 30.9 |
| Polyol 3[f] | 9 | W | 38 | 50 | Insoluble | pH: 3.99<br>1.66 Acid to OH ratio<br>Catalyst: 9.03% Sodium Hypophosphite wrt DS | 13.9 | 30.9 |
| Polyol 3[f] | 10 | W | 35 | 48 | Insoluble | pH: 3.99<br>1.66 Acid to OH ratio<br>Catalyst: 9.03% Sodium Hypophosphite wrt DS | 13.9 | 30.9 |
| Polyol 5[c] | 12 | X | 50 | 62 | Insoluble | pH: 1.61<br>1.66 Acid to OH ratio<br>Catalyst: 8.99% Sodium Hypophosphite wrt DS | 17.2 | 30.8 |
| Polyol 5[c] | 13 | X | 50 | 59 | Insoluble | pH: 1.61<br>1.66 Acid to OH ratio<br>Catalyst: 8.99% Sodium Hypophosphite wrt DS | 17.2 | 30.8 |
| Polyol 5[d] | 14 | Y | 50 | 65 | Insoluble | pH: 2.16<br>1.66 Acid to OH ratio<br>Catalyst: 8.99% Sodium Hypophosphite wrt DS | 17.2 | 30.8 |
| Polyol 5[d] | 15 | Y | 48 | 61 | Insoluble | pH: 2.16<br>1.66 Acid to OH ratio<br>Catalyst: 8.99% Sodium Hypophosphite wrt DS | 17.2 | 30.8 |
| Oligomer FDCA:Polyol 1 (0.6:1) | 16 | Z | 53 | 65 | Insoluble | pH: 2.80<br>1.66 Acid to OH ratio<br>Catalyst: 9.00% Sodium Hypophosphite wrt DS | 11.8 | 30.9 |
| Oligomer FDCA:Polyol 1 (0.6:1) | 17 | Z | 50 | 58 | Insoluble | pH: 2.80<br>1.66 Acid to OH ratio<br>Catalyst: 9.00% Sodium Hypophosphite wrt DS | 11.8 | 30.9 |
| Oligomer FDCA:Polyol 1 (0.7:1) | 19 | AA | 45 | 53 | Insoluble | pH: 2.80<br>1.66 Acid to OH ratio<br>Catalyst: 9.09% Sodium Hypophosphite wrt DS | 11.0 | 30.9 |
| Oligomer FDCA:Polyol 1 (0.7:1) | 20 | AA | 44 | 50 | Insoluble | pH: 2.80<br>1.66 Acid to OH ratio<br>Catalyst: 9.09% Sodium Hypophosphite wrt DS | 11.0 | 30.9 |
| Polyol 3[g] | 21 | BB | 50 | 58 | Insoluble | pH: 3.31<br>1.66 Acid to OH ratio<br>Catalyst: 9.02% Sodium Hypophosphite wrt DS | 16.0 | 1.66 |

TABLE B-6-continued

Stroke-Cure Test Results with FDCA-Based Polyols on 180° C. Hot Plate 7th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 3[g] | 22 | BB | 44 | 52 | Insoluble | pH: 3.31<br>1.66 Acid to OH ratio<br>Catalyst: 9.02% Sodium Hypophosphite wrt DS | 16.0 | 1.66 |
| Malic Acid + Polyol 2 (1:2) | 23 | CC | 48 | 63 | Soluble | pH: 3.09<br>1.65 Acid to OH ratio<br>Catalyst: 8.80% Sodium Hypophosphite wrt DS | 10.2 | 30.9 |
| Malic Acid + Polyol 2 (1:2) | 24 | CC | 48 | 61 | Soluble | pH: 3.09<br>1.65 Acid to OH ratio<br>Catalyst: 8.80% Sodium Hypophosphite wrt DS | 10.2 | 30.9 |
| Oligomer FDCA:Polyol 1 (0.6:1) | 25 | S | 70 | 95 | Soluble | pH: 2.54<br>1.70 Acid to OH ratio<br>Catalyst: 8.97% Sodium Hypophosphite wrt DS<br>%50 Succinic Acid | 6.1 | 31.1 |
| Oligomer FDCA:Polyol 1 (0.6:1) | 26 | S | 72 | 97 | Soluble | pH: 2.54<br>1.70 Acid to OH ratio<br>Catalyst: 8.97% Sodium Hypophosphite wrt DS<br>%50 Succinic Acid | 6.1 | 31.1 |
| Polyol 1 | 27 | DD | 50 | 64 | Soluble | pH: 2.16<br>1.66 Acid to OH ratio<br>Catalyst: 9.09% Sodium Hypophosphite wrt DS | 16.1 | 30.9 |
| Polyol 1 | 28 | DD | 45 | 58 | Soluble | pH: 2.16<br>1.66 Acid to OH ratio<br>Catalyst: 9.09% Sodium Hypophosphite wrt DS | 16.1 | 30.9 |

[a]1. All mixtures required pre-heating to solubilize except for mixture R, Q, CC, S, and DD. 2. All pH measurements were performed with a pH meter calibrated at pH 4 and 7. 3. Unless stated otherwise, all cured binders solidified when cooled. 4. Polyol 1, other than that in DD, was ~85% di-substituted with diethanolamine and N-methyl-N-ethanolamine was used to complete amidification. 5. In calculating Acid/OH ratio, assumed that all reactions went to completion.
[b]Performed by stroke/cure test while allowing mixture to pre-volatize approximately 10 seconds before stroking started.
[c]FDME + Glycerin (1:2 mole ratio) with BF3 catalyst and no removal of excess glycerin.
[d]FDME + Glycerin (1:2 mole ratio) with BF3 catalyst, neutralized, and no removal of excess glycerin.
[e]FDME + Triethanolamine (1:1.8 mole ratio) with BF3 catalyst and no removal of excess triethanolamine.
[f]FDME + Triethanolamine (1:1.8 mole ratio) with BF3 catalyst, neutralized, and no removal of excess triethanolamine.
[g]FDME + Triethanolamine (1:2.2 mole ratio) with BF3 catalyst and no removal of excess triethanolamine.
wrt = with respect to

TABLE B-7

Stroke-Cure Test Results with FDCA-Based Polyols on 180° C. Hot Plate 8th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.6:1) | 7 | XX | — | 330 | Insoluble | pH: 2.89<br>1.66 Acid to OH ratio<br>Catalyst: 9.18% Sodium Hypophosphite wrt DS<br>100% Citric Acid | 0 | 30.9 |
| Oligomer FDCA:Polyol 1 (0.6:1) | 8 | XX | — | 335 | Insoluble | pH: 2.89<br>1.66 Acid to OH ratio<br>Catalyst: 9.18% Sodium Hypophosphite wrt DS<br>100% Citric Acid | 0 | 30.9 |
| Oligomer FDCA:Polyol 1 (0.6:1) + 25% TriEtOHN wrt mole OH | 11 | QQ | 44 | 58 | Insoluble | pH: 3.70<br>1.67 Acid to OH ratio<br>Catalyst: 9.28% Sodium Hypophosphite wrt DS | 12.8 | 30.9 |
| Oligomer FDCA:Polyol 1 (0.6:1) + 25% TriEtOHN wrt mole OH | 12 | QQ | 46 | 59 | Insoluble | pH: 3.70<br>1.67 Acid to OH ratio<br>Catalyst: 9.28% Sodium Hypophosphite wrt DS | 12.8 | 30.9 |
| Polyol 3[c] | 13 | RR | 42 | 52 | Insoluble | pH: 3.97<br>1.67 Acid to OH ratio<br>Catalyst: 9.02% Sodium Hypophosphite wrt DS | 13.1 | 30.9 |
| Polyol 3[c] | 14 | RR | 41 | 50 | Insoluble | pH: 3.97<br>1.67 Acid to OH ratio<br>Catalyst: 9.02% Sodium Hypophosphite wrt DS | 13.1 | 30.9 |
| Polyol 3[d] | 15 | SS | 30 | 41 | Insoluble | pH: 4.52<br>1.67 Acid to OH ratio<br>Catalyst: 9.02% Sodium Hypophosphite wrt DS | 19.1 | 44.9 |

TABLE B-7-continued

Stroke-Cure Test Results with FDCA-Based Polyols on 180° C. Hot Plate 8th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 3[d] | 16 | SS | 32 | 42 | Insoluble | pH: 4.48<br>1.67 Acid to OH ratio<br>Catalyst: 9.02% Sodium Hypophosphite wrt DS | 19.1 | 44.9 |
| Polyol 3[d] | 17 | TT | 20 | 35 | Insoluble | pH: 4.48<br>1.67 Acid to OH ratio<br>Catalyst: 9.02% Sodium Hypophosphite wrt DS | 23.4 | 55.0 |
| Polyol 3[d] | 18 | TT | 21 | 33 | Insoluble | pH: 4.52<br>1.67 Acid to OH ratio<br>Catalyst: 9.02% Sodium Hypophosphite wrt DS | 23.4 | 55.0 |
| Malic Acid + Polyol 1 (1:1) | 20 | EE | — | 45 | Insoluble | pH: 3.15<br>1.66 Acid to OH ratio<br>Catalyst: 9.06% Sodium Hypophosphite wrt DS<br>Starting to cure in hot water | 11.6 | 30.9 |
| Malic Acid + Polyol 1 (1:1) | 21 | EE | — | 42 | Insoluble | pH: 3.15<br>1.66 Acid to OH ratio<br>Catalyst: 9.06% Sodium Hypophosphite wrt DS<br>Starting to cure in hot water | 11.6 | 30.9 |
| Oligomer FDCA:Polyol 1 (0.6:1) | 22 | FF | 44 | 55 | Insoluble | pH: 3.40<br>1.67 Acid to OH ratio<br>Catalyst: 9.11% Sodium Hypophosphite wrt DS | 11.5 | 30.9 |
| Oligomer FDCA:Polyol 1 (0.6:1) | 23 | FF | 45 | 57 | Insoluble | pH: 3.40<br>1.67 Acid to OH ratio<br>Catalyst: 9.11% Sodium Hypophosphite wrt DS | 11.5 | 30.9 |
| Oligomer FDCA:Polyol 1 (0.6:1) | 24 | GG | 30 | 45 | Insoluble | pH: 3.55<br>1.67 Acid to OH ratio<br>Catalyst: 9.11% Sodium Hypophosphite wrt DS | 16.7 | 44.9 |
| Oligomer FDCA:Polyol 1 (0.6:1) | 25 | GG | 32 | 48 | Insoluble | pH: 3.55<br>1.67 Acid to OH ratio<br>Catalyst: 9.11% Sodium Hypophosphite wrt DS | 16.7 | 44.9 |
| Oligomer FDCA:Polyol 1 (0.6:1) | 26 | HH | 29 | 43 | Insoluble | pH: 3.52<br>1.67 Acid to OH ratio<br>Catalyst: 9.11% Sodium Hypophosphite wrt DS | 21.6 | 58.4 |
| Oligomer FDCA:Polyol 1 (0.6:1) | 27 | HH | 30 | 45 | Insoluble | pH: 3.52<br>1.67 Acid to OH ratio<br>Catalyst: 9.11% Sodium Hypophosphite wrt DS | 21.6 | 58.4 |
| Oligomer FDCA:Polyol 1 (0.6:1) | 28 | II | 45 | 60 | Insoluble | pH: 3.58<br>1.20 Acid to OH ratio<br>Catalyst: 9.33% Sodium Hypophosphite wrt DS | 9.3 | 31.0 |
| Oligomer FDCA:Polyol 1 (0.6:1) | 29 | II | 47 | 61 | Insoluble | pH: 3.58<br>1.20 Acid to OH ratio<br>Catalyst: 9.33% Sodium Hypophosphite wrt DS | 9.3 | 31.0 |
| Oligomer FDCA:Polyol 1 (0.6:1) | 30 | JJ | 35 | 55 | Insoluble | pH: 3.74<br>1.20 Acid to OH ratio<br>Catalyst: 9.33% Sodium Hypophosphite wrt DS | 13.5 | 45.0 |
| Oligomer FDCA:Polyol 1 (0.6:1) | 31 | JJ | 34 | 53 | Insoluble | pH: 3.74<br>1.20 Acid to OH ratio<br>Catalyst: 9.33% Sodium Hypophosphite wrt DS | 13.5 | 45.0 |
| Oligomer FDCA:Polyol 1 (0.6:1) | 33 | KK | 25 | 48 | Insoluble | pH: Too thick<br>1.20 Acid to OH ratio<br>Catalyst: 9.33% Sodium Hypophosphite wrt DS | 17.9 | 59.6 |
| Oligomer FDCA:Polyol 1 (0.6:1) | 34 | KK | 27 | 49 | Insoluble | pH: Too thick<br>1.20 Acid to OH ratio<br>Catalyst: 9.33% Sodium Hypophosphite wrt DS | 17.9 | 59.6 |
| Oligomer FDCA:Polyol 1 (0.6:1) | 35 | LL | 55 | 85 | Insoluble | pH: 3.82<br>0.61 Acid to OH ratio<br>Catalyst: 9.63% Sodium Hypophosphite wrt DS | 5.6 | 31.0 |
| Oligomer FDCA:Polyol 1 (0.6:1) | 36 | LL | 56 | 87 | Insoluble | pH: 3.82<br>0.61 Acid to OH ratio<br>Catalyst: 9.63% Sodium Hypophosphite wrt DS | 5.6 | 31.0 |
| Oligomer FDCA:Polyol 1 (0.6:1) | 37 | MM | 59 | 90 | Insoluble | pH: 3.90<br>0.59 Acid to OH ratio<br>Catalyst: 9.10% Sodium Hypophosphite wrt DS | 8.1 | 44.9 |
| Oligomer FDCA:Polyol 1 (0.6:1) | 38 | MM | 55 | 85 | Insoluble | pH: 3.90<br>0.59 Acid to OH ratio<br>Catalyst: 9.10% Sodium Hypophosphite wrt DS | 8.1 | 44.9 |
| Oligomer FDCA:Polyol 1 (0.6:1) | 39 | NN | 38 | 63 | Insoluble | pH: Too thick<br>0.59 Acid to OH ratio<br>Catalyst: 9.10% Sodium Hypophosphite wrt DS | 10.8 | 59.9 |
| Oligomer FDCA:Polyol 1 (0.6:1) | 40 | NN | 45 | 67 | Insoluble | pH: Too thick<br>0.59 Acid to OH ratio<br>Catalyst: 9.10% Sodium Hypophosphite wrt DS | 10.8 | 59.9 |

TABLE B-7-continued

Stroke-Cure Test Results with FDCA-Based Polyols on 180° C. Hot Plate 8th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.6:1) | 41 | OO | 65 | 95 | Insoluble | pH: 3.65<br>0.46 Acid to OH ratio<br>Catalyst: 8.73% Sodium Hypophosphite wrt DS | 4.5 | 30.9 |
| Oligomer FDCA:Polyol 1 (0.6:1) | 42 | OO | 68 | 98 | Insoluble | pH: 3.65<br>0.46 Acid to OH ratio<br>Catalyst: 8.73% Sodium Hypophosphite wrt DS | 4.5 | 30.9 |
| Oligomer FDCA + Citric Acid + Polyol 1 (0.45:0.10:1) | 43 | PP | — | 50 | Insoluble | pH: 3.41<br>1.67 Acid to OH ratio<br>Catalyst: 8.91% Sodium Hypophosphite wrt DS | 11.7 | 30.8 |
| Oligomer FDCA + Citric Acid + Polyol 1 (0.45:0.10:1) | 44 | PP | 35 | 40 | Insoluble | pH: 3.41<br>1.67 Acid to OH ratio<br>Catalyst: 8.91% Sodium Hypophosphite wrt DS | 11.7 | 30.8 |

[a]1. It is believed that all materials were insoluble due to approximately 17% mole amount of the half ester of diethanolamine/half amide by-product present in the Polyol 1; this Polyol 1 was used to make all oligomers tested in this round. 2. All pH measurements were performed with a pH meter calibrated at pH 4 and 7. 3. Unless stated otherwise, all cured binders solidified when cooled. 4. All Polyol 1 was ~85% di-substituted with diethanolamine N-methyl-N-ethanolamine was used to complete amidification. 6. In calculating Acid/OH ratio, assumed that all reactions went to completion.
[b]Performed by stroke/cure test while allowing mixture to pre-volatilize approximately 10 seconds before stroking started.
[c]FDME + Triethanolamine (1:1.5 mole ratio) with BF3 catalyst and no removal of excess triethanolamine.
[d]FDME + Triethanolamine (1:1.5 mole ratio) with BF3 catalyst, neutralized, and no removal of excess triethanolamine.
wrt = with respect to

TABLE B-8

Stroke-Cure Test Results with FDCA-Based Polyols on 180° C. Hot Plate 9th Round[a]

| Composition | Run No. | Notation Mixture | String Time[b] (sec) | Cure Time[b] (sec) | Solubility at Ambient Temperature | Comments | % PAA | % DS |
|---|---|---|---|---|---|---|---|---|
| Polyol 1 | 3 | YY | 48 | 70 | Soluble | pH: 2.64<br>1.66 Acid to OH ratio<br>Catalyst: 9.12% Sodium Hypophosphite wrt DS | 16.2 | 31.0 |
| Polyol 1 | 4 | YY | 50 | 67 | Soluble | pH: 2.64<br>1.66 Acid to OH ratio<br>Catalyst: 9.12% Sodium Hypophosphite wrt DS | 16.2 | 31.0 |
| Polyol 1 | 5 | ZZ | 55 | 72 | Soluble | pH: 2.58<br>1.66 Acid to OH ratio<br>Catalyst: 2.99% Sodium Hypophosphite wrt DS | 17.3 | 30.9 |
| Polyol 1 | 6 | ZZ | 53 | 73 | Soluble | pH: 2.58<br>1.66 Acid to OH ratio<br>Catalyst: 2.99% Sodium Hypophosphite wrt DS | 17.3 | 30.9 |
| Malic Acid + Polyol 1 (1:1) | 7 | AAA | — | 47 | Soluble | pH: 2.89<br>1.66 Acid to OH ratio<br>Catalyst: 9.09% Sodium Hypophosphite wrt DS | 12.1 | 30.9 |
| Malic Acid + Polyol 1 (1:1) | 8 | AAA | — | 48 | Soluble | pH: 2.89<br>1.66 Acid to OH ratio<br>Catalyst: 9.09% Sodium Hypophosphite wrt DS | 12.1 | 30.9 |
| Oligomer FDCA:Polyol 1 (0.6:1) | 9 | BBB | 51 | 59 | Soluble | pH: 2.70<br>1.66 Acid to OH ratio<br>Catalyst: 9.09% Sodium Hypophosphite wrt DS | 12.0 | 31.0 |
| Oligomer FDCA:Polyol 1 (0.6:1) | 10 | BBB | 50 | 58 | Soluble | pH: 2.70<br>1.66 Acid to OH ratio<br>Catalyst: 9.09% Sodium Hypophosphite wrt DS | 12.0 | 31.0 |
| Oligomer FDCA:Polyol 1 (0.6:1) | 11 | CCC | 45 | 55 | Soluble | pH: 2.91<br>1.66 Acid to OH ratio<br>Catalyst: 9.09% Sodium Hypophosphite wrt DS | 15.5 | 40.1 |
| Oligomer FDCA:Polyol 1 (0.6:1) | 12 | CCC | 46 | 54 | Soluble | pH: 2.91<br>1.66 Acid to OH ratio<br>Catalyst: 9.09% Sodium Hypophosphite wrt DS | 15.5 | 40.1 |
| Oligomer FDCA:Polyol 1 (0.6:1) | 13 | DDD | 38 | 47 | Soluble | pH: 3.05<br>1.66 Acid to OH ratio<br>Catalyst: 8.87% Sodium Hypophosphite wrt DS | 19.4 | 49.9 |
| Oligomer FDCA:Polyol 1 (0.6:1) | 14 | DDD | 39 | 48 | Soluble | pH: 3.05<br>1.66 Acid to OH ratio<br>Catalyst: 8.87% Sodium Hypophosphite wrt DS | 19.4 | 49.9 |

TABLE B-8-continued

Stroke-Cure Test Results with FDCA-Based Polyols on 180° C. Hot Plate 9th Round[a]

| Composition | Notation Run No. | Notation Mixture | String Time[b] (sec) | Cure Time[b] (sec) | Solubility at Ambient Temperature | Comments | % PAA | % DS |
|---|---|---|---|---|---|---|---|---|
| Oligomer FDCA:Polyol 1 (0.6:1) | 15 | EEE | 50 | 61 | Soluble | pH: 2.95<br>1.20 Acid to OH ratio<br>Catalyst: 9.23% Sodium Hypophosphite wrt DS | 9.8 | 30.9 |
| Oligomer FDCA:Polyol 1 (0.6:1) | 16 | EEE | 52 | 64 | Soluble | pH: 2.95<br>1.20 Acid to OH ratio<br>Catalyst: 9.23% Sodium Hypophosphite wrt DS | 9.8 | 30.9 |

[a]1. All mixtures were homogeneous. 2. All pH measurements were performed with a pH meter calibrated at pH 4 and 7. 3. Unless stated otherwise, all cured binders solidified when cooled. 4. In calculating Acid/OH ratio, assumed that all reactions went to completion.
[b]Performed by stroke/cure test while allowing mixture to pre-volatilize approximately 10 seconds before stroking started.
wrt = with respect to Table C is a summary table of the more informative tests provided in Tables B-1 through B-8 and is organized so that cure data for polyols 1-5 and the oligomers of polyol 1 are presented in a combined fashion. Table C also provides additional experimental conditions, than found in Tables B-1 through B-8.

TABLE C

Summary of Relevant Binder Compositions and Stroke/Cure Test Results with PAA at 180° C.

| Binder Polyol or Oligomer | Identification Table No. | Identification Run No.// Mixture | Average Cure Times in Stroke/Cure Test (sec.) | Solubility at Ambient Temperature[a] | Wt. % PAA | % DS | Acid/ OH Ratio | pH[b] |
|---|---|---|---|---|---|---|---|---|
| Polyol 1 | | | | | | | | |
| Polyol 1[d] | B-1a | 3, 4//2a | 84 | All soluble | 17.1 | 30.9 | 1.66 | 2-3 |
| Polyol 1[d] | B-1a | 5, 6//2b | 87 | All soluble | 17.4 | 29.4 | 1.66 | 2-3 |
| Polyol 1[e] | B-6 | 27, 28//DD | 61 | All soluble | 16.1 | 30.9 | 1.66 | 2.16 |
| Polyol 1[f] | B-8 | 3, 4//YY | 69 | All soluble | 16.2 | 31.0 | 1.66 | 2.64 |
| Polyol 1[f] | B-8 | 5, 6//ZZ | 73 | All soluble | 17.3 | 30.9 | 1.66 | 2.58 |
| Polyol 1[f] | B-5 | 13, 14//U | ~185 | All soluble | None | 30.8 | 1.65 | 1.54 |
| Polyol 1[d] | B-1a | 7//3 | No Cure | All soluble | None | 23.6 | — | 2-3 |
| Oligomers of Polyol 1 and FDCA | | | | | | | | |
| Oligomer (1:1) FDCA:Polyol 1[d] | B-1b | 7, 8//6 | 76 | Insolubles | 7.70 | 23.1 | 1.65 | 2.5-3 |
| Oligomer (1:1) FDCA:Polyol 1[d] + Polyol 4 (10% wt. wrt oligomer | B-2 | 5, 6/A | 61 | Insolubles | 5.40 | 23.3 | 0.46 | 3 |
| Oligomer (0.9:1) FDCA:Polyol 1[e] | B-2 | 7, 8//E | 66 | Insolubles | 7.70 | 23.0 | 1.11 | 2.5-3 |
| Oligomer (0.9:1) FDCA:Polyol 1[e] + Polyol 4 (5% wt. wrt oligomer | B-4 | 12, 13//I | 57 | Insolubles | 13.2 | 30.9 | 1.65 | 2-3 |
| Oligomer (0.8:1) FDCA:Polyol 1[f] | B-3 | 5, 6//K | 83 | All soluble | 14.5 | 30.9 | 1.65 | 2-3 |
| Oligomer (0.7:1) FDCA:Polyol 1[f] | B-4 | 13, 14//J | 57 | All soluble | 15.1 | 30.9 | 1.65 | 2-3 |
| Oligomer (0.7:1) FDCA:Polyol 1[f] | B-6 | 19, 20//AA | 52 | Insolubles | 11.0 | 30.9 | 1.65 | 2.80 |
| Oligomer (0.6:1) FDCA:Polyol 1[f] | B-5 | 7, 8//R | 57 | All soluble | 11.8 | 30.9 | 1.66 | 2.53 |
| Oligomer (0.6:1) FDCA:Polyol 1[f] | B-6 | 16, 17//Z | 62 | Insolubles | 11.8 | 30.9 | 1.66 | 2.80 |
| Oligomer (0.6:1) FDCA:Polyol 1[f] | B-8 | 9, 10//BBB | 59 | All soluble | 12.0 | 31.0 | 1.66 | 2.70 |
| Oligomer (0.6:1) FDCA:Polyol 1[f] | B-8 | 15, 16//EEE | 63 | All soluble | 9.8 | 30.9 | 1.20 | 2.95 |
| Oligomer (0.6:1) FDCA:Polyol 1[f] | B-8 | 11, 12//CCC | 55 | All soluble | 15.5 | 40.1 | 1.66 | 2.91 |
| Oligomer (0.6:1) FDCA:Polyol 1[f] | B-8 | 13, 14//DDD | 48 | All soluble | 19.4 | 49.9 | 1.66 | 3.05 |
| Oligomer (0.6:1) FDCA:Polyol 1[f] | B-6 | 25, 26//S | 96 | All soluble | 6.1 | 31.1 | 1.70 | 2.54 |

TABLE C-continued

Summary of Relevant Binder Compositions and Stroke/Cure Test Results with PAA at 180° C.

Oligomer of Polyol 1 and Malic Acid

| | | | | | | | | |
|---|---|---|---|---|---|---|---|---|
| Oligomer (1:1) Malic A.:Polyol 1[f] | B-8 | 7, 8//AAA | 46 | All soluble | 12.1 | 30.9 | 1.66 | 2.89 |

Oligomer of Polyol 2 and Malic Acid

| | | | | | | | | |
|---|---|---|---|---|---|---|---|---|
| Oligomer (1:2) Malic A.:Polyol 2 | B-6 | 23, 24//CC | 62 | All soluble | 10.2 | 30.9 | 1.65 | 3.09 |

Polyol 3

| | | | | | | | | |
|---|---|---|---|---|---|---|---|---|
| Polyol 3 | B-6 | 5, 6//Q | 53 | All soluble | 13.9 | 30.9 | 1.66 | 3.36 |
| Polyol 3 | B-6 | 7, 8//V | 51 | Insolubles | 13.9 | 30.9 | 1.66 | 3.56 |
| Polyol 3 | B-6 | 9, 10//W | 49 | Insolubles | 13.9 | 30.9 | 1.66 | 3.99 |
| Polyol 3 | B-6 | 21, 22//BB | 55 | Insolubles | 16.0 | 30.9 | 1.66 | 3.31 |

Polyol 4

| | | | | | | | | |
|---|---|---|---|---|---|---|---|---|
| Polyol 4 | B-1b | 3, 4//5 | 66 | Insolubles | 19 | 30.9 | 1.65 | 2-3 |

Polyol 5

| | | | | | | | | |
|---|---|---|---|---|---|---|---|---|
| Polyol 5 | B-1b | 5, 6//4 | 80 | Insolubles | 17.1 | 30.9 | 2.03 | 1 |
| Polyol 5 | B-2 | 9, 10//B | 85 | Insolubles | 16.3 | 26.2 | 1.66 | 1-2 |
| Polyol 5 | B-4 | 9, 10//O | 69 | All soluble | 21.5 | 30.9 | 1.66 | 1-2 |
| Polyol 5 | B-5 | 3, 4//P | 64 | All soluble | 17.2 | 30.9 | 1.65 | 1.08 |
| Polyol 5 | B-6 | 12, 13//X | 61 | Insolubles | 17.2 | 30.8 | 1.66 | 1.61 |
| Polyol 5 | B-6 | 14, 15//Y | 63 | Insolubles | 17.2 | 30.8 | 1.66 | 2.16 |

| Binder Polyol or Oligomer | Comments[c] |
|---|---|

Polyol 1

| | |
|---|---|
| Polyol 1[d] | 6.91% $NaH_2PO_2$; Stroking started after 20 sec. |
| Polyol 1[d] | No catalyst; Stroking started after 20 sec. |
| Polyol 1[e] | 9.09% $NaH_2PO_2$; Stroking started after 10 sec. |
| Polyol 1[f] | 9.12% $NaH_2PO_2$; Stroking started after 10 sec. |
| Polyol 1[f] | 2.99% $NaH_2PO_2$; Stroking started after 10 sec. |
| Polyol 1[f] | 100% replacement of PAA with malic acid; 8.95% $NaH_2PO_2$ |
| Polyol 1[d] | No PAA; No catalyst |

Oligomers of Polyol 1 and FDCA

| | |
|---|---|
| Oligomer (1:1) FDCA:Polyol 1[d] | 6.90% $NAH_2PO_2$; Prepared by Oligomer of Polyol 1 and FDCA Method 3 as described in Preparation Methods (with the exception of 30 minutes total reaction time). |
| Oligomer (1:1) FDCA:Polyol 1[d] + Polyol 4 (10% wt. wrt oligomer | 2.59% $NAH_2PO_2$; Prepared by Oligomer of Polyol 1 and FDCA Method 3 as described in Preparation Methods (with the exception of 30 minutes total reaction time). |
| Oligomer (0.9:1) FDCA:Polyol 1[e] | 3.59% $NaH_2PO_2$; Prepared by Oligomer of Polyol 1 and FDCA Method 3 as described in Preparation Methods. |
| Oligomer (0.9:1) FDCA:Polyol 1[e] + Polyol 4 (5% wt. wrt oligomer | 3.10% $NaH_2PO_2$; Prepared by Oligomer of Polyol 1 and FDCA Method 3 as described in Preparation Methods. |
| Oligomer (0.8:1) FDCA:Polyol 1[f] | 4.80% $NaH_2PO_2$; Prepared by Oligomer of Polyol 1 and FDCA Method 2 as described in Preparation Methods. |
| Oligomer (0.7:1) FDCA:Polyol 1[f] | 4.55% $NaH_2PO_2$; Prepared by Oligomer of Polyol 1 and FDCA Method 1 as described in Preparation Methods. |
| Oligomer (0.7:1) FDCA:Polyol 1[f] | 9.09% $NaH_2PO_2$; Prepared by Oligomer of Polyol 1 and FDCA Method 2 as described in Preparation Methods. |
| Oligomer (0.6:1) FDCA:Polyol 1[f] | 9.20% $NaH_2PO_2$; Prepared by Oligomer of Polyol 1 and FDCA Method 1 as described in Preparation Methods. |
| Oligomer (0.6:1) FDCA:Polyol 1[f] | 9.00% $NaH_2PO_2$; Prepared by Oligomer of Polyol 1 and FDCA Method 2 as described in Preparation Methods. |
| Oligomer (0.6:1) FDCA:Polyol 1[f] | 9.09% $NaH_2PO_2$; Prepared by Oligomer of Polyol 1 and FDCA Method 1 as described in Preparation Methods. |
| Oligomer (0.6:1) FDCA:Polyol 1[f] | 9.23% $NaH_2PO_2$; Prepared by Oligomer of Polyol 1 and FDCA Method 1 as described in Preparation Methods. |
| Oligomer (0.6:1) FDCA:Polyol 1[f] | 99.09% $NaH_2PO_2$; Prepared by Oligomer of Polyol 1 and FDCA Method 1 as described in Preparation Methods. Increased viscosity compared to mixture EEE. |
| Oligomer (0.6:1) FDCA:Polyol 1[f] | 8.87% $NaH_2PO_2$; Prepared by Oligomer of Polyol 1 and FDCA Method 1 as described in Preparation Methods. Increased viscosity compared to mixture CCC. |

TABLE C-continued

Summary of Relevant Binder Compositions and Stroke/Cure Test Results with PAA at 180° C.

| | |
|---|---|
| Oligomer (0.6:1) FDCA:Polyol 1[f] | 50% replacement of PAA with succinic acid; 8.97% $NaH_2PO_2$; Prepared by Oligomer of Polyol 1 and FDCA Method 1 as described in Preparation Methods. |

Oligomer of Polyol 1 and Malic Acid

| | |
|---|---|
| Oligomer (1:1) Malic A.:Polyol 1[f] | 9.09% $NaH_2PO_2$; Preparation of oligomer did not involve removal of either reagent. |

Oligomer of Polyol 2 and Malic Acid

| | |
|---|---|
| Oligomer (1:2) Malic A.:Polyol 2 | 8.80% $NaH_2PO_2$; Preparation of oligomer did not involve removal of excess polyol 2. |

Polyol 3

| | |
|---|---|
| Polyol 3 | 9.04% $NaH_2PO_2$; Polyol 3 was prepared from FDCA dimethyl ester FDME + triethanolamine (TEA) (1:1.8 mole ratio) using $BF_3$ as catalyst; TEA & $BF_3$ were not removed. |
| Polyol 3 | 9.03% $NaH_2PO_2$; Same preparation as above; longer heating than Mixture Q. |
| Polyol 3 | 9.03% $NaH_2PO_2$; Same oligomer used in V but $BF_3$ was removed. |
| Polyol 3 | 9.02% $NaH_2PO_2$; Polyol 3 was prepared from FDME + TEA (1:2.2 mole ratio) using $BF_3$ as catalyst; TEA & $BF_3$ were not removed. |

Polyol 4

| | |
|---|---|
| Polyol 4 | 7.69% $NaH_2PO_2$; All material was solubilized by preheating to 65° C. |

Polyol 5

| | |
|---|---|
| Polyol 5 | 6.90% $NaH_2PO_2$; polyol 5 was prepared from FDCA + glycerin (1:4 mole ratio) with no catalyst; excess glycerin was removed by distillation. All material was solubilized by preheating to 75° C. |
| Polyol 5 | 2.09% $NaH_2PO_2$; polyol 5 was prepared from FDCA + glycerin (1:2.25 mole ratio) using $NaH_2PO_2$ as catalyst; excess glycerin was not removed. |
| Polyol 5 | 9.16% $NaH_2PO_2$; polyol 5 was prepared from FDME + glycerin (1:1.8 mole ratio) using $BF_3$ as catalyst; excess glycerin was not removed. |
| Polyol 5 | 8.96% $NaH_2PO_2$; polyol 5 was prepared from FDME + glycerin (1:2 mole ratio) using $BF_3$ as catalyst; excess glycerin and BF3 were not removed. |
| Polyol 5 | 8.99% $NaH_2PO_2$; polyol 5 was prepared from FDME + glycerin (1:2 mole ratio) using $BF_3$ as catalyst; excess glycerin was not removed. |
| Polyol 5 | 8.99% $NaH_2PO_2$; polyol 5 was prepared from FDME + glycerin (1:2 mole ratio) using $BF_3$ as catalyst; BF3 was removed but excess glycerin was not. |

[a]Mixtures labeled "Insolubles" required warming to solubilize all components.
[b]pH of fully formulated binder solutions were measured either with colorpHast ® paper or pH meter before curing (values obtained from a pH meter are indicated by three decimal places).
[c]$NaH_2PO_2$ concentrations are expressed as weight percentages relative to the amount of "dry solids" (materials other than water).
[d]Polyol 1 was prepared by Method 1 in Preparation Section and consists of 83 mole percent FDCA bisamide of diethanolamine and the balance of FDCA mixed methyl ester/monoamide of diethanolamine.
[e]Polyol 1 was prepared by Method 2 in Preparation Section and consists of 75 mole percent FDCA bisamide of diethanolamine and 25 mole percent mixed FDCA mixed amide/methyl ester.
[f]Polyol 1 was prepared by Method 3 in Preparation Section and consists of 71 mole percent FDCA bisamide of diethanolamine, 10 mole percent of FDCA mixed bisamide of diethanolamine and 2-(methylamino)ethanol and 18% mixed FDCA amide/methyl ester..

The results of these curing tests are summarized below:

The following discussion are based on data developed for Polyols 1-5 and include conclusions that can be drawn from the composition data and stroke/cure test results for polyols 1-5 and oligomers of polyol 1 that are summarized in Table C.

Polyol 1

Polyol 1 is the FDCA bisamide of diethanolamine and has four pendant hydroxyl groups. It can be seen that all aqueous binder solutions of polyol 1 and PAA were soluble. As seen in the Table C, polyol 1 was either a mixture of approximately 83% FDCA bisamide of diethanolamine and 17% FDCA methyl ester/monoamide of diethanolamine, 75% FDCA bisamide of diethanolamine and 25% FDCA methyl ester/monoamide of diethanolamine, or was a mixture of 71% FDCA bisamide of diethanolamine, 10% FDCA mixed bisamide of diethanolamine and 2-(methylamino)ethanol, and 18% FDCA methyl ester/monoamide of diethanolamine. It can be seen by comparing Run Numbers//Mixtures 3,4//2a versus 5,6//2b and Run Numbers//Mixtures 3,4//YY and 5,6//ZZ that polyol 1 cured at about the same rate with the esterification catalyst sodium hypophosphite and when this catalyst was absent or significantly decreased. This behavior is characteristic of esterification reactions of the hydroxyl groups of beta-hydroxyethylamides that are generally believed not to require acidic catalysts. The lowest cure time observed with polyol 1 having the composition indicated by footnote e was 61 seconds (Run Number//Mixture 27,28//DD whose composition contained the highest amount of hypophosphite catalyst and shortest delay in stroking time). The lowest cure time observed with Polyol 1 having the composition indicated in footnote f was 69 seconds (Run Number//Mixture 3,4//YY). Polyol 1 underwent a significantly slower cure when malic acid, a monomeric dicarboxylic acid, was used in the presence of hypophosphite but this data indicates that polyol 1 curing is still feasible with monomeric dicarboxylic acids. Polyol 1 did not cure when both PAA and hypophosphite were excluded, indicating that curing of these systems by potential etherification reactions did not occur. It can be seen that the pH values of polyol 1 samples cured with PAA were typically in the 2-3 range.

Oligomers of Polyol 1 and FDCA

A range of oligomers with a range of mole ratios of FDCA to polyol 1 in the presence of PAA were prepared and evaluated by stroke/cure tests and these results are tabulated in Table C. It can be seen that FDCA/polyol 1 oligomers prepared with 1:1 through 0.6:1 mole ratios had cure times that were comparable to or shorter than the cure times of polyol 1 itself. These results were obtained even when the percent dry solid contents of these oligomers were lower than the percent dry solid content of polyol 1 and(or) the sodium hypophosphite catalyst concentrations were lower than those used with polyol 1. Addition of small quantities of polyol 4, a hexaol expected to provide efficient crosslinking, to the 1:1 and 0.9:1 oligomers led to significantly reduced curing times (Run Numbers//Mixtures 5,6//A and 12,13I) compared to the 1:1 and 0.9:1 oligomers themselves. It can be seen that the pH of these oligomers were typically in the 2.5-2.8 range.

Aqueous compositions containing 1:1 and 0.9:1 oligomers plus PAA were found to have insoluble material that could be solubilized by warming these mixtures. However, certain FDCA/polyol 1 oligomers ranging from 0.8:1 to 0.6:1 mole ratios in the presence of PAA were soluble in water when prepared in about the same concentrations (Run Numbers//Mixtures 5,6//K; 13,14//J; and 7,8//R). These increased water solubilities are presumed to result from the increased proportion of hydroxyl groups provided in oligomers by polyol 1 as the oligomeric FDCA/polyol 1 molar ratios are decreased. Of interest, it was found that whereas 0.7:1 FDCA/polyol 1 oligomer Run Number//Mixture 13,14//J was water soluble, the 0.7:1 FDCA/polyol 1 oligomer Run Number//Mixture 19,20//M was insoluble. This latter 0.7:1 oligomer was purposely prepared with extended esterification reaction times and it is presumed that the reduced aqueous solubility was caused by generation of an oligomer with more extensive crosslinking. Similarly, whereas the 0.6:1 FDCA/polyol 1 oligomer Run Number//Mixture 7,8//R was water soluble, the 0.6:1 FDCA/Polyol 1 oligomer Run Number//Mixture 16,17//Z had insoluble components. Again, it is presumed that this aqueous solubility difference was due to the fact that the esterification reaction time and stirring efficiency was greater in the latter esterification reaction resulting in increased oligomer crosslinking and decreased water solubility. Comparison of Run Numbers//Mixtures 9,10//BBB and 15,16//EEE shows that the amount of PAA as expressed by the Acid/OH ratio can be reduced from the most typical value evaluated (1.66) to 1.20 while causing a relatively minor increase in cure times from 59 to 63 seconds and also an increase in binder pH. Experiments were also performed wherein the Acid/OH ratio of 1.66 was maintained but the percent dry solids (% DS) was increased from 31% to 40% to 50% (Run Numbers//Mixtures 15,16//EEE; 11,12//CCC; and 13,14//DDD) while noting the cure times decreased from 63 seconds to 55 seconds to 48 seconds and the pH values changed from 2.95 to 2.91 to 3.05 It was also found that 50% replacement of PAA with the dicarboxylic acid succinic acid led to an increase in cure times but these results do indicate that monomeric diacids can be used to cure polyol-based binder compositions, either as mixtures with PAA or potentially by themselves.

Oligomer of Polyol 1 and Malic Acid

An oligomer of malic acid, a biobased dicarboxylic acid that also contains one hydroxyl group, and polyol 1 (a tetrahydroxylic FDCA bisamide derivative) was prepared by esterifying malic acid with Polyol 1 in a malic acid:polyol 1 mole ratio of 1:1. This esterification composition is expected to result in relatively short oligomers having pendant hydroxyl groups derived from polyol 1 as well as the hydroxyl groups present on each malic acid entity that would both lead to increased water solubility. As can be seen in Table C a mixture of this composition and the appropriate amount of PAA had the shortest cure times observed in this overall study (46 seconds) and it also had a relatively high pH value of 2.89.

Oligomer of Polyol 2 and Malic Acid

An oligomer of malic acid, a biobased dicarboxylic acid that also contains one hydroxyl group, and polyol 2 (a dihydroxylic FDCA derivative) was prepared by esterifying malic acid with polyol 2 in a malic acid:polyol 2 ratio of 1:2 mole ratio. This esterification composition is expected to result in relatively short oligomers having pendant hydroxyl groups derived from polyol 2 as well as the hydroxyl groups present on each malic acid entity that would both lead to increased water solubility. It can be seen in Table C that a mixture of this composition and the appropriate amount of PAA had cure times comparable to those of polyol 1 and its oligomers with FDCA. Further, this composition was water soluble and it had a relatively high pH value of 3.09.

Polyol 3

Polyol 3 is the ester of FDCA and triethanolamine and has four pendant hydroxyl groups as well as two amine nitrogen atoms that are expected to moderate the acidity of solutions containing PAA. Polyol 3 was prepared by transesterification of FDCA dimethyl ester with an excess of triethanolamine. It can be seen that the cure times for all polyol 3 entries with PAA were in the 49-55 second range which are generally shorter than those observed for polyol 1 and its oligomers with FDCA. Of interest, it was found that Run Number//Mixture 5,6//Q was water soluble whereas Run Number//Mixture 7,8//V contained insoluble material that required warming to generate a soluble solution. The main difference between these two compositions was that longer reaction times were used in preparing the former composition compared to the reaction times used to prepare the latter composition. The possible reason for the different aqueous solubilities of these two compositions is that the extended reaction times caused a greater degree of reaction between monoesterified FDCA moieties and fully esterified FDCA systems, resulting in increased crosslinking. The pH values of all polyol 3/PAA compositions were the highest of all polyol/PAA compositions tested in the 3.4-4.0 range.

Polyol 4

Polyol 4 is the FDCA bisamide of tris(hydroxymethyl)aminomethane (Tris), has six pendant hydroxyl groups, and was prepared by transesterfication of FDCA dimethyl ester with an excess of Tris. The one preparation of polyol 4 (Run Number//Mixture 3,4//5) was assumed to have appreciable crosslinking due to the fact that it contained insoluble material that required warming to generate a homogeneous solution. This mixture has a cure time of 66 seconds and a pH in the 2-3 range.

Polyol 5

Polyol 5 is a mixture of FDCA glyceride esters that include FDCA bis(1-monoglyceride) shown above but also FDCA-based diglycerides and potentially triglycerides. Selective preparation of FDCA bis(1-monoglyceride) will be favored by using an excess of glycerin in esterification or transesterification reactions and FDCA-based diglycerides and triglycerides will be favored by using lower relative quantities of glycerin. The performance properties of polyol 5 prepared with different amounts of glycerin relative to FDCA-based starting materials are provided in Table C. Cure times in general were found to be comparable to those obtained with other polyols 1-4 and oligomers of polyols 1 and 2. It can be seen that all polyol 5/PAA mixtures had relatively low pH values and that are believed to primarily result from residual FDCA carboxylic acid groups or acidic esterification or transesterification catalysts remaining in these mixtures. Developing synthetic methods that led to complete reaction of residual FDCA carboxylic acid groups would result in reduced binder mixture acidities. It can be seen that the highest pH values determined in Run Number//Mixture 14,15//Y (2.2) was obtained by removing the acidic catalyst $BF_3$ used as a transesterification catalyst in its preparation.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A binder composition comprising an oligomer or polymer of a reaction product of
   a. a polyol selected from the group consisting of polyol 1, polyol 2, polyol 3, polyol 4, and polyol 5, wherein polyols 1-5 have the formula of

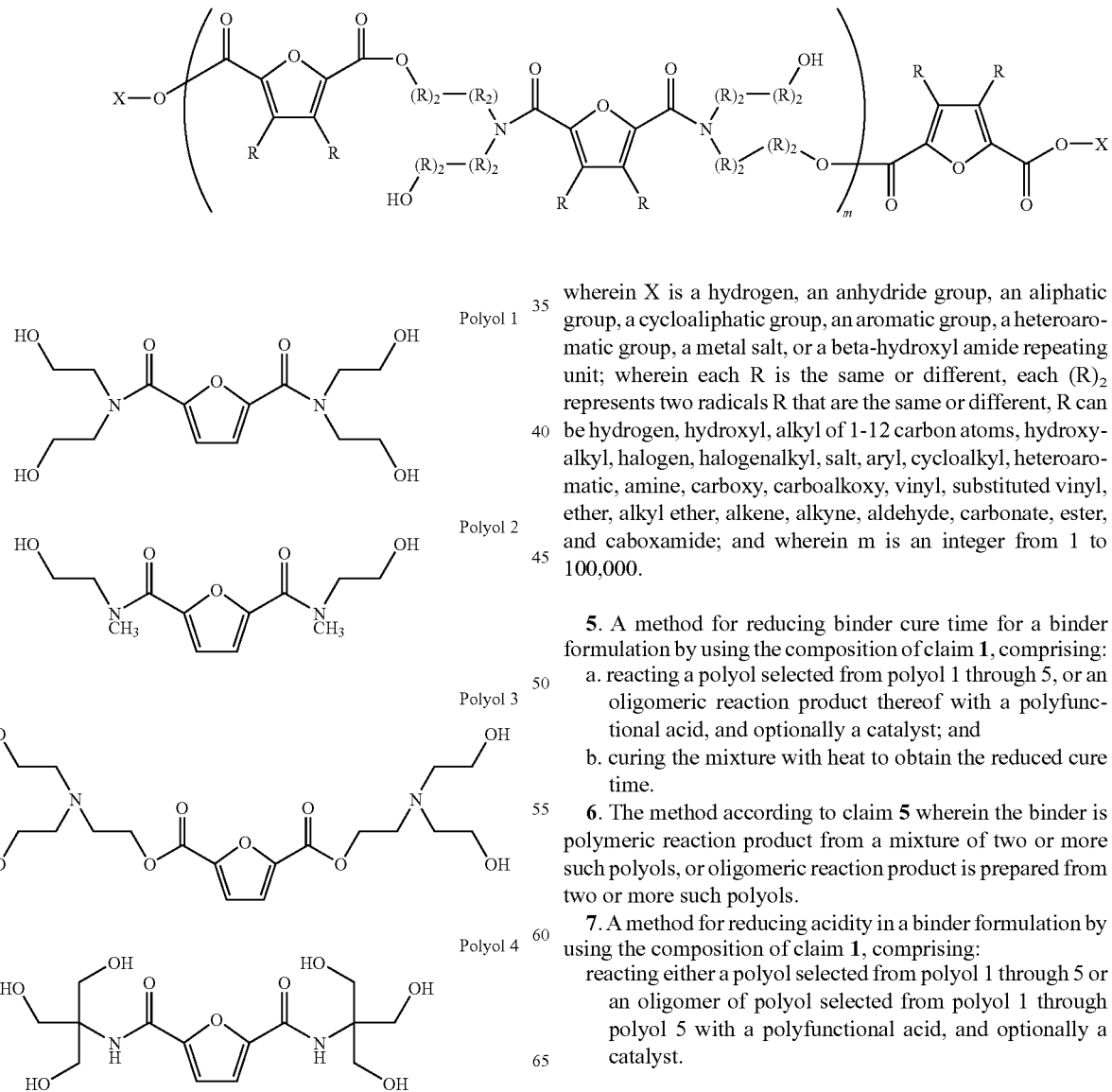

b. a polyfunctional acid or a polyfunctional nitrile.

2. The oligomer or polymer according to claim 1 wherein the polyfunctional acid is a diacid.

3. The oligomer or polymer according to claim 1, wherein the polyfunctional acid is selected from the group of acids consisting of FDCA, malic acid, citric acid, maleic acid, oxalic acid, malonic acid, succinic acid, itaconic acid, fumeric acid, and mixtures thereof.

4. A polymeric composition comprising wherein X is a hydrogen, an anhydride group, an aliphatic group, a cycloaliphatic group, an aromatic group, a heteroaromatic group, a metal salt, or a beta-hydroxyl amide repeating unit; wherein each R is the same or different, each $(R)_2$ represents two radicals R that are the same or different, R can be hydrogen, hydroxyl, alkyl of 1-12 carbon atoms, hydroxyalkyl, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, and caboxamide; and wherein m is an integer from 1 to 100,000.

5. A method for reducing binder cure time for a binder formulation by using the composition of claim 1, comprising:
   a. reacting a polyol selected from polyol 1 through 5, or an oligomeric reaction product thereof with a polyfunctional acid, and optionally a catalyst; and
   b. curing the mixture with heat to obtain the reduced cure time.

6. The method according to claim 5 wherein the binder is polymeric reaction product from a mixture of two or more such polyols, or oligomeric reaction product is prepared from two or more such polyols.

7. A method for reducing acidity in a binder formulation by using the composition of claim 1, comprising:
   reacting either a polyol selected from polyol 1 through 5 or an oligomer of polyol selected from polyol 1 through polyol 5 with a polyfunctional acid, and optionally a catalyst.

* * * * *